United States Patent
Barron et al.

(10) Patent No.: US 11,541,135 B2
(45) Date of Patent: *Jan. 3, 2023

(54) MULTIPLE BAND VISIBLE LIGHT DISINFECTION

(71) Applicant: Vyv, Inc., Latham, NY (US)

(72) Inventors: Robert Barron, Boulder, CO (US); James Peterson, Falls Church, VA (US); Cori Winslow, Rensselaer, NY (US)

(73) Assignee: Vyv, Inc., Latham, NY (US)

( * ) Notice: Subject to any disclaimer, the term of this patent is extended or adjusted under 35 U.S.C. 154(b) by 388 days.

This patent is subject to a terminal disclaimer.

(21) Appl. No.: 16/456,715

(22) Filed: Jun. 28, 2019

(65) Prior Publication Data

US 2020/0405893 A1  Dec. 31, 2020

(51) Int. Cl.
*A61L 2/00* (2006.01)
*F21K 9/64* (2016.01)
*F21Y 115/10* (2016.01)

(52) U.S. Cl.
CPC .............. *A61L 2/0052* (2013.01); *F21K 9/64* (2016.08); *A61L 2202/14* (2013.01); *F21Y 2115/10* (2016.08)

(58) Field of Classification Search
CPC ....... A61L 2/0052; F21K 9/64; F21Y 2115/10
See application file for complete search history.

(56) References Cited

U.S. PATENT DOCUMENTS

| | | |
|---|---|---|
| 1,493,820 A | 5/1924 | Miller et al. |
| 2,622,409 A | 12/1952 | Stimkorb |
| 2,773,715 A | 12/1956 | Lindner |
| 3,314,746 A | 4/1967 | Millar |
| 3,670,193 A | 6/1972 | Thorington et al. |
| 3,791,864 A | 2/1974 | Steingroever |
| 3,926,556 A | 12/1975 | Boucher |
| 3,992,646 A | 11/1976 | Corth |
| 4,121,107 A | 10/1978 | Bachmann |
| 4,461,977 A | 7/1984 | Pierpoint et al. |
| 4,576,436 A | 3/1986 | Daniel |
| 4,867,052 A | 9/1989 | Cipelletti |
| 4,892,712 A | 1/1990 | Robertson et al. |
| 4,910,942 A | 3/1990 | Dunn et al. |
| 5,231,472 A | 7/1993 | Marcus et al. |

(Continued)

FOREIGN PATENT DOCUMENTS

| | | |
|---|---|---|
| CN | 201396611 Y | 2/2010 |
| CN | 201423033 Y | 3/2010 |

(Continued)

OTHER PUBLICATIONS

Jul. 23, 2020—(TW) Office Action w/TR—TW 108148627.

(Continued)

*Primary Examiner* — Kevin Joyner

(74) *Attorney, Agent, or Firm* — Banner & Witcoff, Ltd.

(57) ABSTRACT

Systems and methods for multiple band visible light disinfection are disclosed. In some examples, a disinfecting light is generated by combining two different disinfecting wavelength ranges of light. A lighting device may comprise a first light source that generates light in a Soret band. The lighting device may further comprise a second light source that generates light in a Q band. The light in the Soret band and the light in the Q band may be combined to generate disinfecting light.

16 Claims, 22 Drawing Sheets

(56) References Cited

U.S. PATENT DOCUMENTS

| | | |
|---|---|---|
| 5,489,827 A | 2/1996 | Xia |
| 5,530,322 A | 6/1996 | Ference et al. |
| 5,559,681 A | 9/1996 | Duarte |
| 5,668,446 A | 9/1997 | Baker |
| 5,721,471 A | 2/1998 | Begemann et al. |
| 5,725,148 A | 3/1998 | Hartman |
| 5,800,479 A | 9/1998 | Thiberg |
| 5,901,564 A | 5/1999 | Comeau, II |
| 5,962,989 A | 10/1999 | Baker |
| 6,031,958 A | 2/2000 | McGaffigan |
| 6,166,496 A | 12/2000 | Lys et al. |
| 6,183,500 B1 | 2/2001 | Kohler |
| 6,242,752 B1 | 6/2001 | Soma et al. |
| 6,246,169 B1 | 6/2001 | Pruvot |
| 6,251,127 B1 | 6/2001 | Biel |
| 6,379,022 B1 | 4/2002 | Amerson et al. |
| 6,477,853 B1 | 11/2002 | Khorram |
| 6,524,529 B1 | 2/2003 | Horton, III |
| 6,551,346 B2 | 4/2003 | Crossley |
| 6,554,439 B1 | 4/2003 | Teicher et al. |
| 6,627,730 B1 | 9/2003 | Burnie |
| 6,676,655 B2 | 1/2004 | McDaniel |
| 6,791,259 B1 | 9/2004 | Stokes et al. |
| 6,902,807 B1 | 6/2005 | Argoitia et al. |
| 7,015,636 B2 | 3/2006 | Bolta |
| 7,175,807 B1 | 2/2007 | Jones |
| 7,190,126 B1 | 3/2007 | Paton |
| 7,198,634 B2 | 4/2007 | Harth et al. |
| 7,201,767 B2 | 4/2007 | Bhullar |
| 7,213,941 B2 | 5/2007 | Sloan et al. |
| 7,438,719 B2 | 10/2008 | Chung et al. |
| 7,503,675 B2 | 3/2009 | Demarest et al. |
| 7,516,572 B2 | 4/2009 | Yang et al. |
| 7,521,875 B2 | 4/2009 | Maxik |
| 7,611,156 B2 | 11/2009 | Dunser |
| 7,612,492 B2 | 11/2009 | Lestician |
| 7,658,891 B1 | 2/2010 | Barnes |
| 7,955,695 B2 | 6/2011 | Argoitia |
| 8,035,320 B2 | 10/2011 | Sibert |
| 8,214,084 B2 | 7/2012 | Ivey et al. |
| 8,232,745 B2 | 7/2012 | Chemel et al. |
| 8,357,914 B1 | 1/2013 | Caldwell |
| 8,398,264 B2 | 3/2013 | Anderson et al. |
| 8,476,844 B2 | 7/2013 | Hancock et al. |
| 8,481,970 B2 | 7/2013 | Cooper et al. |
| 8,506,612 B2 | 8/2013 | Ashdown |
| 8,508,204 B2 | 8/2013 | Deurenberg et al. |
| 8,761,565 B1 | 6/2014 | Coleman et al. |
| 8,886,361 B1 | 11/2014 | Harmon et al. |
| 8,895,940 B2 | 11/2014 | Moskowitz et al. |
| 8,999,237 B2 | 4/2015 | Tumanov |
| 9,024,276 B2 | 5/2015 | Pugh et al. |
| 9,027,479 B2 | 5/2015 | Raksha et al. |
| 9,028,084 B2 | 5/2015 | Maeng et al. |
| 9,039,966 B2 | 5/2015 | Anderson et al. |
| 9,046,227 B2 | 6/2015 | David et al. |
| 9,078,306 B2 | 7/2015 | Mans et al. |
| 9,119,240 B2 | 8/2015 | Nagazoe |
| 9,173,276 B2 | 10/2015 | Van Der Veen et al. |
| 9,257,059 B2 | 2/2016 | Raksha et al. |
| 9,283,292 B2 | 3/2016 | Kretschmann |
| 9,313,860 B2 | 4/2016 | Wingren |
| 9,323,894 B2 | 4/2016 | Kiani |
| 9,333,274 B2 | 5/2016 | Peterson et al. |
| 9,368,695 B2 | 6/2016 | David et al. |
| 9,410,664 B2 | 8/2016 | Krames et al. |
| 9,420,671 B1 | 8/2016 | Sugimoto et al. |
| 9,433,051 B2 | 8/2016 | Snijder et al. |
| 9,439,271 B2 | 9/2016 | Ku et al. |
| 9,439,989 B2 | 9/2016 | Lalicki et al. |
| 9,492,576 B1 | 11/2016 | Cudak et al. |
| 9,581,310 B2 | 2/2017 | Wu et al. |
| 9,623,138 B2 | 4/2017 | Pagan et al. |
| 9,625,137 B2 | 4/2017 | Li et al. |
| 9,681,510 B2 | 6/2017 | van de Ven |
| 10,806,812 B2 | 10/2020 | Barron et al. |
| 2002/0074559 A1 | 6/2002 | Dowling et al. |
| 2002/0122743 A1 | 9/2002 | Huang |
| 2003/0009158 A1 | 1/2003 | Perricone |
| 2003/0019222 A1 | 1/2003 | Takahashi et al. |
| 2003/0023284 A1 | 1/2003 | Gartstein et al. |
| 2003/0124023 A1 | 7/2003 | Burgess et al. |
| 2003/0178632 A1 | 9/2003 | Hohn et al. |
| 2003/0231485 A1 | 12/2003 | Chien |
| 2004/0008523 A1 | 1/2004 | Butler |
| 2004/0010299 A1 | 1/2004 | Tolkoff et al. |
| 2004/0024431 A1 | 2/2004 | Carlet |
| 2004/0039242 A1 | 2/2004 | Tolkoff et al. |
| 2004/0047142 A1 | 3/2004 | Goslee |
| 2004/0147984 A1 | 7/2004 | Altshuler et al. |
| 2004/0147986 A1 | 7/2004 | Baumgardner et al. |
| 2004/0158541 A1 | 8/2004 | Notarianni et al. |
| 2004/0159039 A1 | 8/2004 | Yates et al. |
| 2004/0162596 A1 | 8/2004 | Altshuler et al. |
| 2004/0230259 A1 | 11/2004 | Di Matteo |
| 2004/0262595 A1 | 12/2004 | Mears et al. |
| 2004/0266546 A1 | 12/2004 | Huang |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2005/0159795 A1 | 7/2005 | Savage et al. |
| 2005/0207159 A1 | 9/2005 | Maxik |
| 2005/0212397 A1 | 9/2005 | Murazaki et al. |
| 2005/0253533 A1 | 11/2005 | Lys et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0278927 A1 | 11/2008 | Li et al. |
| 2008/0305004 A1 | 12/2008 | Anderson et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0262515 A1 | 10/2009 | Lee et al. |
| 2009/0285727 A1 | 11/2009 | Levy |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |

(56) References Cited

U.S. PATENT DOCUMENTS

| | | |
|---|---|---|
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2014/0043810 A1 | 2/2014 | Jo et al. |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0015840 A1 | 1/2016 | Gordon |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0354502 A1 | 12/2016 | Simmons et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0124883 A1 | 5/2018 | Bailey |
| 2018/0139817 A1 | 5/2018 | Yamakawa et al. |
| 2018/0180226 A1 | 6/2018 | Van Bommel et al. |

FOREIGN PATENT DOCUMENTS

| | | |
|---|---|---|
| CN | 102213382 A | 10/2011 |
| CN | 105304801 A | 2/2016 |
| CN | 105339094 A | 2/2016 |
| CN | 205360038 U | 7/2016 |
| CN | 106937461 A | 7/2017 |
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| KR | 20130096965 A | 9/2013 |
| KR | 101526261 B1 | 6/2015 |
| KR | 101648216 B1 | 8/2016 |
| KR | 20160127469 A | 11/2016 |
| KR | 101799538 B1 | 11/2017 |
| TW | M268106 U | 6/2005 |
| TW | 201412240 A | 4/2014 |
| TW | M530654 U | 10/2016 |
| TW | 201831977 A | 9/2018 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016019029 A1 | 2/2016 |
| WO | 2016068285 A1 | 5/2016 |
| WO | 2016209632 A1 | 12/2016 |
| WO | 2017009534 A1 | 1/2017 |
| WO | 2017205578 A1 | 11/2017 |
| WO | 2019108432 A1 | 6/2019 |

OTHER PUBLICATIONS

Jul. 6, 2020—(WO) ISR & WO—App PCT/US2019/068799.
Absorption and Fluorescence Spectroscopy of Tetraphenylporphyrin§ and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four-Orbital Model of Gouterman, article, Sep. 8, 2009, 7 pp., Protein & Peptide Letters, 2010, vol. 17, No. 4, Department of Biology, Faculty of Sciences, Shahid Chamran University of Ahvaz, Tehran, Iran.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2, 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, 9 pp., vol. 20, No. 6, 2002, Journal of Clinical LaserMedicine & Surgery, Canada.
Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and

(56) References Cited

OTHER PUBLICATIONS

Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U. K.
Jun. 29, 2018—(DE) Office Action—App 112016003453.9.
Nov. 27, 2018—(JP) Office Action—JP 2018-525520.
Jan. 4, 2019—(TW) Office Action—App 104124977.
Apr. 15, 2019—(CA) Examiner's Report—App 2,993,825.
Nov. 5, 2019—(JP) Final Office Action—JP 2018-525520.
Oct. 9, 2019—(CN) Office Action—CN 201680048598.9.
Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Jun. 1, 2020—(GB) Examiner's Report—App GB1802648.4.
Apr. 14, 2020—(TW) 2nd Office Action—App 107143577 (w/translation).
May 12, 2020—(JP) Final Office Action—JP 2018-525520.
NuTone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90.
NuTone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809.
NuTone, "Ultra Pro™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca.
Papageorgiou, P. et al., "Phototherapy with Blue (415 nm) and Red (660 nm) Light in the Treatment of Acne Vulgaris," British Journal of Dermatology, 2000, pp. 973-978.
Pelz, A. et al., "Structure and biosynthesis of staphyloxanthin production of methicillin-resistant *Staphylococcus aureus*," Bioi. Pharm. Bull., 2012, val. 35, No. 1, 9 pages.
Pochi, P.E., "Acne: Androgens and microbiology," Drug Dev, Res., 1988, val. 13, 4 pages, abstract only provided.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214.
Reed, "The History of Ultraviolet Germicidal Irradiation for Air Disinfection," Public Health Reports, Jan.-Feb. 2010, vol. 125, 13 pages.
Sakai, K., et al., "Search for inhibitors of staphyloxanthin production by methicillin-resistant *Staphylococcus aureus*," Biol. Pharm. Bull., 2012, val. 35, No. 1, pp. 48-53.
Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio. 3 pages.
Sikora, A. et al., "Lethality of visable light for *Escherichia coli*hemH 1 mutants influence of defects in DNA repair," DNA Repair, 2, pp. 61-71.
Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 6 pages.
Soraa, "PAR30L 18.5W," retrieved from the Internet on Apr. 20, 2017 at: http://www.soraa.com/products, 5 pages.
Soraa, "PAR30L," retrieved from the Internet on Apr. 20, 2017 at: http://www_soraa.com/products/22-PAR30L, 6 pages.
Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tong, Y. et al., "Solar radiation is shown to select for pigmented bacteria in the ambient outdoor atmosphere," Photochemistry and Photobiology, 1997, val. 65, No. 1, pp. 103-106.
Tong, Y., et al. "Population study of atmospheric bacteria at the Fengtai district of Beijing on two representative days," Aerobiologica, 1993, vol. 9, 1 page, Abstract only provided.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://lwww.researchgate.net/publication/304628914.
Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, Aug. 1981, pp. 410-417.
Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.
Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE.
Ward, "Experiments on the Action of Light on Bacillus anthracis," 10 pages.
Wilson et al., "Killing of methicillin-resistant *Staphylococcus aureus* by low-power laser light," J. Med, Microbial., vol. 42 (1995), pp. 62-66.
Yi, Notice of Allowance and Fee(s) due for U.S. Appl. No. 14/501,931 dated Jan. 20, 2016, 8 pages.
Yoshimura et al., "Antimicrobial effects of phototherapy and photochemotherapy in vivo and in vitro," British Journal of Dermatology, 1996, 135: 528-532.
Yu, J. et al., "Efficient Visible-Light-Induced Photocatalytic Disinfection on Sulfur-Doped Nanocrystalline Titania," Environ. Sic. Technol., 39, 2005, pp. 1175-1179.
Oct. 31, 2008—(WO) ISR & WO—App PCT/GB2008/003679.
May 4, 2010—(WO) IPRP—App PCT/GB2008/003679.
Nov. 2, 2015—(WO) WO & ISR—App PCT/US2015/042678.
Dec. 8, 2016—(WO) ISR & WO—App PCT/US2016/036704.
Oct. 20, 2016—(WO) ISR & WO—App PCT/US2016/44634.
Apr. 16, 2018—(WO) ISR & WO—App PCT/US2017/068755.
Mar. 6, 2018—(WO) ISR & WO—App PCT/US2017/068749.
Feb. 11, 2019—(WO) ISR—App PCT/US2018/061859.
Feb. 28, 2019—(WO) ISR—App PCT/US2018/061843.
Feb. 28, 2019—(WO) ISR—App PCT/US2018/061856.
Jul. 8, 2019—(WO) ISR & WO—App PCT/US2019/024593.
Ashkenazi, H. et al., "Eradication of Propionibacterium acnes by its endogenic porphyrins after illumination with high intensity blue light," FEMS Immunology and Medical Microbiology, 35, pp. 17-24.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76.
Bek-Thomsen, M., "Acne is Not Associated with Yet-Uncultured Bacteria," J. Clinical Microbial., 2008, 46{10), 9 pages.
Berezow Alex, How to Kill Insects With Visible Light, Real Clear Science, Jan. 11, 2015, pp. 1-4, <https://www.realclearscience.com/journal_club/2015/01/12/how_to_kill_insects_with_visible_light_109021.html>.
Burchard, R. et al., "Action Spectrum for Carotenogenesis in Myxococcus xanthus," Journal of Bateriology, 97(3), 1969, pp. 1165-1168.
Burkhart, C. G. et al., "Acne: a review of immunologic and microbiologic factors," Postgraduate Medical Journal, 1999, vol. 75, pp. 328-331.
Burkhart, C. N. et al., "Assesment of etiologic agents in acne pathogenesis," Skinmed, 2003, vol. 2, No. 4, pp. 222-228.

(56) References Cited

OTHER PUBLICATIONS

Chukuka et al., Visible 405 nm SLD light photo-destroys metchicillin-resistant *Staphylococcus aureus* {MRSA} in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.

Clauditz, A. et al., "Staphyloxanthin plays a role in the fitness of *Staphylococcus aureus* and its ability to cope with oxidative stress," Infection and Immunity, 2006, vol. 74, No. 8, 7 pages.

Color Phenomena, "CIE-1931 Chromaticity Diagram," last updated Aug. 22, 2013, retrieved from www.color-theory-phenomena.nl/10.02.htm on Jan. 20, 2016, 3 pages.

Dai et al., "Blue light for infectious diseases: Propionibacterium acnes, Helicobacter pylori, and beyond?," Drug Resist Update, 15(4): 223-236 {Aug. 2012).

Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245.

Demidova, T. et al., "Photodynamic Therapy Targeted to Pathogens," International Journal of Immunipathology and Pharmacology, 17(3), pp. 245-254.

Dornob, "Healthy Handle: Self-Sanitizing UV Dorr Knob Kils Germs", Dornob.com, Dec. 5, 2018, pp. 1-3, https://dornob.com/healthy-handle-self-sanitizing-uv-door-knob-kills-germs/.

Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/.

Elman, M. et al., "The Effective Treatment of Acne Vulgaris by a High-intensity, Narrow Band 405-420 nm Light Source," Cosmetic & Laser Ther, 5, pp. 111-116.

Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, http://www.jmest.org/wp-content/uploads/JMESTN42351112.pdf.

Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only.

Guffey et al., "In Vitro Bactericidal Effects of 405-nm and 470-nm Blue Light," Photomedicine and Laser Surgery, vol. 24, No. 6, retrieved from: https:/lwww.liebertpub.com/doi/abs/10.1089/pho.2006.24.684 on Mar. 23, 2018, 2 pages, abstract only provided.

Halstead et al., "The antibacterial activity of blue light against nosocomial wound pathogens growing planktonically and as mature biofilms," Appl. Environ, Microbial., Apr. 2016, 38 pages, retrieved from: http://aem.asm.org/.

Hamblin et al., "Helicobacter pylori Accumulates Photoactive Porphyrins and is Killed by Visable Light," Antimicrobial Agents and Chemotherapy, Jul. 2005, pp. 2822-2827.

Harrison, A.P., "Survival of Bacteria," Annu. Rev. Microbial, 1967, p. 143, vol. 21.

Holzman, "405-nm Light Proves Potent at Decontaminating Bacterial Pathogens," retrieved from: http://forms.asm.org/microbe/index.asp?bid=64254 on Aug. 6, 2015, 34 pages.

Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan. <https://www.semanticscholar.org/paper/Lethal-effects-of-short-wavelength-visible-light-o-Hori-Shibuya/2c11cb3f70a059a051d8ed02fff0e8a9b7a4c4d4>.

Huffman, D. et al., "Inactivation of Bacteria, Virus and Cryptospordium by a Point-of-use Device Using Pulsed Broad Spectrum White Light," Wat. Res. 34(9), pp. 2491-2498.

Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.

Jappe, U., "Pathological mechanisms of acne with special emphasis on Propionibacterium acnes and related therapy," Acta Dermato-Venereologica, 2003, vol. 83, pp. 241-248.

Kawada et al., "Acne Phototherapy with a high-intensity, enhanced, narrow-band, blue light source: an open study and in vitro investigation," Journal of Dermatological Science 30 (2002) pp. 129-135.

Kickstarter, "Orb, The World's First Germ-Killing BLue/UV Light Ball", Dec. 10, 2018, pp. 1-10,<https://www.kickstarter.com/projects/572050089078660/orbtm-the-worlds-first-germ-killing-uv-light-ball>.

Knowles et al., "Near-Ultraviolet Mutagenesis in Superoxide Dismutase-deficient Strains of *Escherichia coli*," Environmental Health Perspectives, vol. 102{1}, Jan. 1994, pp. 88-94.

Kristoff et al., "Loss of photoreversibility for UV mutation in *E. coli* using 405 nm or near-US challenge," Mutat Res., May 1983, 109{2}: 143-153, 2 pages, abstract only provided.

Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012.

LEDs Magazine, "ANSI continues advancements on SSL chromaticity standard," retrieved from the Internet on Apr. 20, 2017 at: http:/lwww.ledsmagazine.com/articles/print/volume-12/issue-11/features/standards/ansi-continues-advancements-on-ssl-chromaticity-standard.html, Published Dec. 8, 2015, 6 pages.

LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.

LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.

LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html. Published Jun. 14, 2007, 2 pages.

Maclean et al., "High-intensity narrow-spectrum light inactivation and wavelength sensitivity of *Staphylococcus auresu*," FEMS Microbial. Lett., vol. 285 (2008) pp. 227-232.

Marshall, J. H., et al., "Pigments of *Staphylococcus au reus*, a series of triterpenoid carotenoids," J. Bacteriology, 1981, vol. 147, No. 3, pp. 900-913.

Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>.

Nov. 30, 2020—(GB) Intent to Grant—GB 1802648.4.

Nov. 6, 2020—(TW) Office Action w/Tr.—TW 108146777.

Dec. 2, 2020—(TW) Rejection Decision—App 108111242 (Eng Trans).

Sep. 29, 2020—(WO) ISR & WO—App PCT/US2020/046504.

Nov. 23, 2020—(WO) ISR & WO—App PCT/US2020/051254.

Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.

Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.

Jul. 21, 2021—(TW) Office Action—TW 108148627.

Aug. 31, 2021—(CN) Office Action—CN 201980033309.1.

MULTIPLE BAND VISIBLE LIGHT DISINFECTION

TECHNICAL FIELD

Aspects of the present disclosure generally relate to processes, systems, and apparatus for visible light disinfection.

BACKGROUND

Bacterial and microorganism inactivation is a crucial practice required in many areas of both personal and environmental hygiene for the benefit of human health. Many methods may be employed for a variety of situations where human health factors may be improved by inactivating bacterial and microorganisms. Sickness and infection are the primary concerns of bacterial or microorganism contamination. The contamination may be caused by the transmission of microorganisms between human beings (e.g., from direct contact) or from a surrounding environment.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure provide methods, devices, and techniques for generation of disinfecting light. One or more aspects of this disclosure relate to generation of disinfecting light based on Soret band and Q bands.

An example light emitting device that inactivates microorganisms on a surface may comprise a first light source operable to emit a first light having a first wavelength in a Soret band at a first intensity sufficient to initiate inactivation of microorganisms, and a second light source operable to emit a second light having a second wavelength in a Q band at a second intensity sufficient to initiate inactivation of microorganisms, wherein the first light and the second light combine to form a disinfecting light.

An example method of inactivating microorganisms may comprise emitting, from a first light source, a first light having a first wavelength in a Soret band at a first intensity sufficient to initiate inactivation of microorganisms, emitting, from a second light source, a second light having a second wavelength in a Q band at a second intensity sufficient to initiate inactivation of microorganisms, and causing the first light and the second light to combine to form a disinfecting light.

An example light emitting device that inactivates microorganisms on a surface may comprise a light emitter operable to emit a first light having a first wavelength in a Soret band at a first intensity sufficient to initiate inactivation of microorganisms on the surface, and a light-converting material arranged to be in a direct path of the first light and operable to convert a first portion of the first light to a second light having a second wavelength in a Q band at a second intensity sufficient to initiate inactivation of microorganisms on the surface, wherein the first light and the second light combine to form disinfecting light.

DETAILED DESCRIPTION

Figure 1:
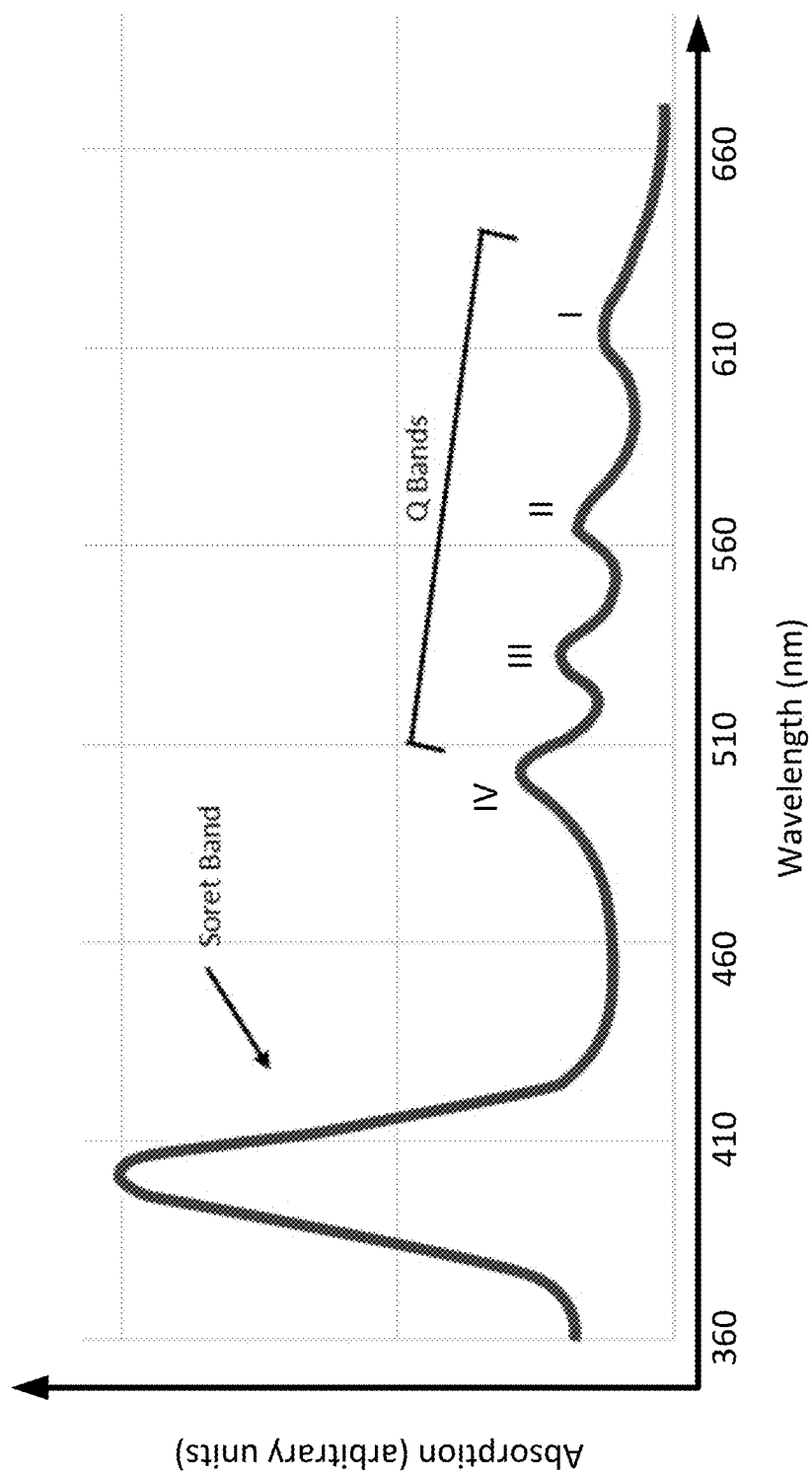
FIG. 1 shows an approximate absorption spectra for a porphyrin molecule, in accordance with one or more examples disclosed herein.

In the following description of the various examples, reference is made to the accompanying drawings, which form a part hereof, and in which are shown by way of illustrations, various examples of the disclosure that may be practiced. It is to be understood that other examples may be utilized.

Microorganism removal protocols play an important role in protecting human health in environments where transmission of microorganisms may cause a higher rate of infection (e.g., healthcare facilities, schools, prisons, mass transit hubs, etc.) because of population density, health factors, specific activities, or other factors. These procedures may range comprise one or more of hand washing protocols, manual cleaning with disinfectants, air circulation requirements, chemical bombing, light-based disinfection technologies, etc.

In other environments, inactivation of microorganisms is desirable due to effects they may have on processes or goods. Foods, pharmaceuticals, biomaterials, or other products and their processes are susceptible to microorganism proliferation, which may cause contamination or loss of goods or public exposure.

Cleaning requirements and work load may become burdensome and costly in situations where consistent cleaning procedures are required for maintaining standard levels of cleanliness. Manual cleaning is extremely costly in terms of materials and labor costs, is prone to human error, and does not result in complete removal of microorganisms. Other procedures, such as chemical bombing and burst ultraviolet (UV) treatment, may only be used in an environment that is preferably isolated from human exposure. UV light, for example, has well-known negative effects on human health. Systems using UV light may often require complicated control systems to ensure there is no accidental exposure to humans.

Procedures and processes for microorganism removal may be operated at a particular frequency for increased and continued effectiveness. Frequency-based cleaning procedures include set cleaning and/or disinfection tasks performed based on a scheduled or reactionary timeline (e.g., mopping at the beginning of a day, wiping down surfaces in the morning and evening every day, etc.). Frequency-based cleaning procedures may include manual cleaning multiple times per day with disinfectants and shutdown of environments for isolation cleaning processes. While a frequency-based cleaning procedure may cause temporary microorganism removal from an environment, microorganisms may immediately re-enter and re-populate the environment as soon as the cleaning procedure is completed. In between such cleaning procedures, these environments become more and more contaminated because of transmission or microorganism growth. This may pose a higher risk of contamination or infection.

It is advantageous in highly sensitive environments (e.g., hospitals) to remove as much bacteria as often as possible for highest potential reduction in contamination or infection. While frequency-based cleaning procedures remove some bacteria from the environments, such procedures, on their own, cannot maintain a consistently decontaminated environment. For example, current procedures of manual cleaning, chemical bombing, and UV treatments reach a limit of usage simply due to complications of interrupting normal facility operations and/or massive labor and material requirements associated with high frequency cleaning. With this limit in mind, it is advantageous to pursue methods of decontamination that may operate consistently to increase bacterial removal and maintain cleaner environments.

Illumination methods may be used for disinfection. Illumination, in general, may be broadly classified into general illumination and non-general illumination. General illumination may be defined as lighting produced to illuminate at least a portion of an indoor area for areas occupied by users (e.g., for enhancing observability of surroundings) and/or that require illumination to complete tasks (e.g., walking, eating, reading, etc.). General illumination devices may include overhead ceiling fixtures, table lamps, floor lamps, task lighting, etc. General illumination is often required to be white light with certain defining characteristics.

Non-general illumination may be defined as lighting produced to illuminate a limited space or internally illuminate an object. It may be used for, for example, aesthetic purposes or as an indicator. Non-general illumination devices may include indicators in backlit buttons, lights in internally illuminated handles, aquarium lights, etc. Non-general illumination may not be required to be a certain color. Non-white light may be applicable in many applications where non-general illumination can be used. Non-white light may also be applicable in indoor areas when an area is not occupied by users or when illumination is not required to complete tasks. In these cases, non-white light may be integrated into general illumination devices as a second mode along with white light.

Visible light disinfection methods disclosed herein, may fulfill needs for continuous decontamination methods that may be used continuously during normal operations and not interrupt activities over the course of the day. The visible light disinfection comprises activating endogenous molecules inside microorganisms that may initiate inactivation through various methods. The visible light disinfection methods, as described this disclosure, may effectively inactivate microorganisms at light intensity levels that are considered safe for human exposure by many regulatory bodies.

One type of visible light disinfection is called single-band disinfection, which focuses on using a single narrow wavelength range with disinfection properties, e.g., 380 nm-420 nm. Other bands of light may also contain disinfecting properties, e.g., 490 nm-660 nm, as well as several others. Each range of light may contain properties that aid disinfection. When various ranges of light are used, in at least some examples, a combination of the various ranges may be more effective than the various ranges being used alone.

Wavelengths of visible light in the violet range, e.g., 380 nm-420 nm, have a lethal effect on microorganisms such as bacteria, yeast, mold, fungi, etc. Examples of bacteria inactivated by this wavelength range are *Escherichia coli* (*E. coli*), *Salmonella*, Methicillin-resistant *Staphylococcus*

*Aureus* (MRSA), and *Clostridium difficile*. These wavelengths of light initiate a photoreaction with porphyrin molecules or porphyrin derivatives found in microorganisms. These porphyrin molecules are photoactivated and react with other cellular components to produce Reactive Oxygen Species (ROS). The ROS causes irreparable cell damage and eventually results in cell death. This same kill mechanism does not work on humans, plants, or animals, because these organisms do not contain the same porphyrin molecules, making this technique completely safe for human exposure. While photosensitive molecules other than porphyrins and porphyrin derivatives exist in microorganisms, current understanding in the field focuses on porphyrin activation due to its relatively high effectiveness at light levels acceptable for human exposure.

Inactivation, in relation to microorganism death, is defined by noted reduction in microorganism colonies or individual cells when exposed to disinfecting light for a certain duration as compared to the same organism, in an identical setup and measured over the same duration, that is not exposed significant amounts of light. The setups shall be identical to an extent realistically practicable by someone skilled in the art with minimally required equipment.

A wavelength range of 380 nm-420 nm is perceived by humans as a dim violet color. A wavelength range of 490 nm-660 nm light may be perceived by humans as a bright green color. Colored lighting may be appropriate for uses other than general illumination (e.g., non-general illumination) or when illumination in a room is not required. A band of light (e.g., a wavelength range of 380 nm-420 nm light) may be combined with another range of light to produce a disinfecting light. Such disinfecting light may have a hue of white light. This method may result in light that may be more acceptable (e.g., than a narrow wavelength, or a single-band light) in at least some circumstances. This type of visible light disinfection may be appropriate for uses other than general illumination or when illumination in a room is not required.

White light that comprises one or more wavelength ranges of visible light, and further comprises wavelength ranges of visible light that have disinfecting properties, may be advantageous, in at least some circumstances, because the complete spectrum may be used as a general illumination source while also resulting in consistent bacterial inactivation. Non-white light that comprises one or more wavelength ranges of visible light, and further comprises wavelength ranges of visible light that have disinfecting properties, may provide an element of customization and aesthetic quality to the light while concurrently providing consistent bacterial inactivation.

Example methods, systems, or devices disclosed herein result in lighting quality improvements in addition to enhanced disinfecting characteristics. Examples disclosed herein relate to the use of different ranges of visible light that correlate to the inactivation of bacteria and other microorganisms. One or more disinfecting wavelength ranges may be combined, for example, to produce high-quality white light, while meeting current standards in lighting quality and offering improved bacterial inactivation rates. The high-quality white light may be used for bacterial inactivation in general illumination systems. One or more disinfecting wavelength ranges may be combined, for example, to produce a non-white light or a hue of white light. The hue of white light or the non-white light may be used for bacterial inactivation in non-general illumination systems.

Example methods, systems, or devices disclosed herein use different regions of the visible light spectrum to initiate microorganism inactivation, including regions of the spectrum different from the 380 nm-420 nm wavelength range. These regions may also, for example, provide methods of bacterial inactivation independently in the same manner as other light-based disinfection methods. These bands may also be mixed with another wavelength to produce a white, a hue of white light, or non-white light, as described in this application. This combination could include, for example, one or more wavelength bands other than the 380 nm-420 nm wavelength band.

It may be advantageous to combine two or more of different ranges of visible light from one or more a light sources. In some examples, a total amount of lumens required may be reduced to offer same or additional decontamination effectiveness by combining two or more different ranges of visible light.

An example lighting device uses at least two different ranges of light, noted to cause microorganism inactivation, combined with possible addition of one or more other ranges of light for light quality to produce white light or a hue of white light. An example lighting device uses at least two different ranges of light, noted to cause microorganism inactivation, combined with possible addition of other ranges of light for color aesthetic to produce a desired non-white light emitted from the light source or light fixture. Example light sources disclosed herein may emit light, in addition to providing visible light disinfection that may be improved by combination methods as described in various examples provided in this disclosure, to cause inactivation of microorganisms on surfaces, air, water, fluids, and gases.

Examples of light sources may include light emitting diodes (LED), organic LEDs (OLEDs), lasers, semiconductor dies, light converting materials, light converting layers, LEDs with light converting material(s)/layer(s), electroluminescent wires, electroluminescent sheets, flexible LEDs, etc. A light source may comprise of a single LED package that may include one or more semiconductor emitter dies within the LED package.

An example device may comprise of a single light source that generates light in multiple wavelength ranges. The single light source may be for example, a light emitter or a light converting material. An example device may comprise two light sources, each light source corresponding to respective one or more wavelength ranges. In some examples, the two light sources may each be emitters generating light in corresponding wavelength ranges. In some examples, one light source may be an emitter corresponding to a first wavelength, and the other light source may be a light converting material. The light converting material may, for example, convert at least a portion of light from the first light source to the second wavelength range.

FIG. 1 shows a visible light absorption spectra graph corresponding to an example porphyrin molecule. Porphyrins have a visible absorption spectrum that is commonly characterized by two peaks or ranges of peaks on the absorption spectra graph. The "Soret" peak is commonly centered between 380 nm-420 nm wavelength range (referred to herein as the Soret band) and may be the most sensitive of the peaks seen in the visible absorption spectra. The second characteristic is a peak or series of peaks that may exist at around the 490 nm-660 nm wavelength range and may be denoted as the "Q band" or "Q bands" or the "Q band region." The Q band characteristically has four peaks, commonly denoted as IV, III, II, and I, with the IV peak being towards the 490 nm end, and the I peak being towards the 660 nm end. These two ranges designate ranges of light which when used are effective in causing microorganism inactivation through exposure to these ranges of light. Porphyrins and their derivatives have relatively similar spectra to that shown in FIG. 1, but may vary based upon structural variations and a solution an absorption spectra was measured in.

Examples disclosed herein include lighting devices comprising one or more light sources emitting light within the visible region of light (380 nm-750 nm). The one or more light sources combine to provide sufficient energy in both the Soret band and Q band absorption regions of a porphyrin molecule, or porphyrin derivative, such that microorganisms containing these molecules will become inactivated.

Some examples disclosed herein comprise one range of emitted light in the Soret band region and an additional range of light in the Q band region or Q band peaks IV-I. By emitting light in both of these regions, microorganism inactivation may be achieved and be more effective than using any single peak to cause the inactivation.

White light is perceived in the human eye by the S, M, and L (short, medium, and long) cones, which react to wavelengths most commonly described as blue, green, and red, respectively. The human eye may perceive white light (or a hue of white light) when the S, M, and L cones are activated using blue, green, and red lights and if the lights are received at appropriate intensities.

Through proper selection of light sources, light sources with peaks at or near the respective peaks at the Soret band and Q bands of the porphyrin may be combined, at proper intensities, to produce a color, for example, that may be perceived by humans as "white." The addition of other wavelengths of light may improve the color rendering index (CRI) (a rating of quality associated with white light) and help aid in the balancing of intensities and wavelength selection required to produce an overall white light. In some examples, the white light may be used to activate the Soret band and at least one of the Q bands.

In various examples described herein, a white light or a non-white light is generated, using both the Soret band and at least one of the Q bands, that may inactivate microorganisms. In various examples, described herein, the light is generated in a manner such that the intensity of the light, at a location (e.g., on a surface, in air, in water, in fluid, or in gas), is sufficient to inactivate microorganisms at the location. The intensity of the light that is sufficient to inactivate microorganisms at the location may depend on a distance of the location from a source of the light. This method creates a light that is more effective in microorganism inactivation than any one wavelength that activates just one of a Soret band or Q band that is mixed with other non-related wavelengths to generate light that may inactivate microorganisms.

In various examples disclosed herein, a combination of light is not chosen to create white light, but instead to produce another color of light with minimum amounts of each band (e.g., the Soret band and at least one of the Q bands) contained within a spectrum corresponding to the non-white light.

Examples disclosed herein comprise a lighting device or fixture emitting sufficient intensity in the 380 nm-420 nm band of light to initiate microorganism cell death and at least one other wavelength band in an alternative range of 490 nm-660 nm at a sufficient intensity to initiate microorganism cell death. Where when these wavelengths are combined with the possible addition of other wavelengths, an overall output of the light emitting device may be perceived as white or a hue of white light by the human eye. LEDs and phosphor conversion technologies serve as suitable methods of light generation as described.

Examples disclosed herein comprise a light-emitting device or fixture emitting sufficient intensity in the 380 nm-420 nm band of light to initiate microorganism cell death and at least one other wavelength band in an alternative range of 490 nm to 660 nm at a sufficient intensity to initiate microorganism cell death. Where when these wavelengths are combined with the possible addition of other wavelengths, an overall output of the light emitting device may be perceived as a non-white color by the human eye. LEDs and phosphor conversion technologies serve as suitable methods of light generation as described.

Efficiencies of various example devices in inactivating bacteria may be a function of radiometric energy content for each of the Soret band and Q band regions as compared to the overall lumens of white light or non-white light produced by the devices. A unit to express this measure may be radiometric watts (of region(s) in question) per lumen. Various example devices in this disclosure provide more radiometric energy per lumen in the Soret and the Q regions combined than a comparable light source using only energy in one of the Q bands and the Soret band for the inactivation of bacteria.

While the Q band region may cause microorganism inactivation, it may have much less efficacy than the Soret band, as may be seen in example porphyrin absorption spectra in FIG. 1. Soret band inactivation is many times more effective in inactivating microorganisms than the Q band region and thus may be valued higher in a white light source or a non-white light source in terms of radiometric content per lumen of white light or non-white light. In at least some examples, it may also be advantageous to combine both Soret band and Q band regions in a white light source or a non-white light source such that a radiometric content in sensitive regions is increased. In at least some examples, it may also be advantageous to combine both Soret band and Q band regions in a white light source such that a CRI of the white light is increased to general illumination standards.

Figure 2:
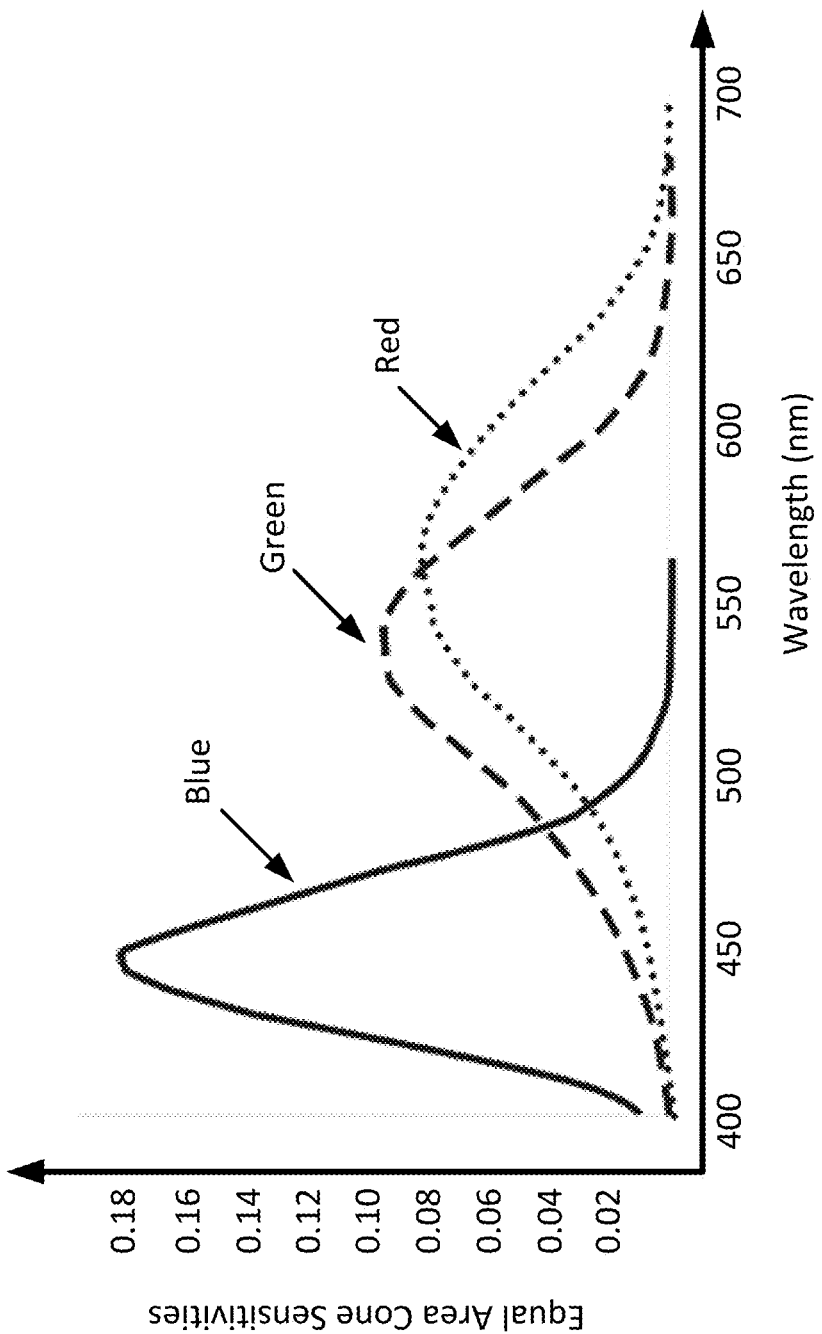
FIG. 2 shows a graph of the sensitivity to different wavelengths of light for the S, M and L cones in the human eye used to interpret color, in accordance with one or more examples disclosed herein.

While a device using common light emitting diode (LED) lighting methods (e.g., RGB, phosphor conversion, etc.) may have a high lumens per watt for electrical efficiency, the heavy reliance on blue diodes to sensitize the S cones of the eye is very effective in illumination due to luminous sensitivity characteristics of light and the human eye. But blue diodes are not very effective in causing microorganism inactivation. FIG. 2 shows equal area cone sensitivities corresponding to cones that are sensitive to blue, green, and red lights. In some examples, a blue component is highly desirable because it is a primary color used in eye sensitivity. It has been demonstrated that the use of blue in some example spectra may improve CRI up to acceptable CRI levels for general illumination.

Figure 3:
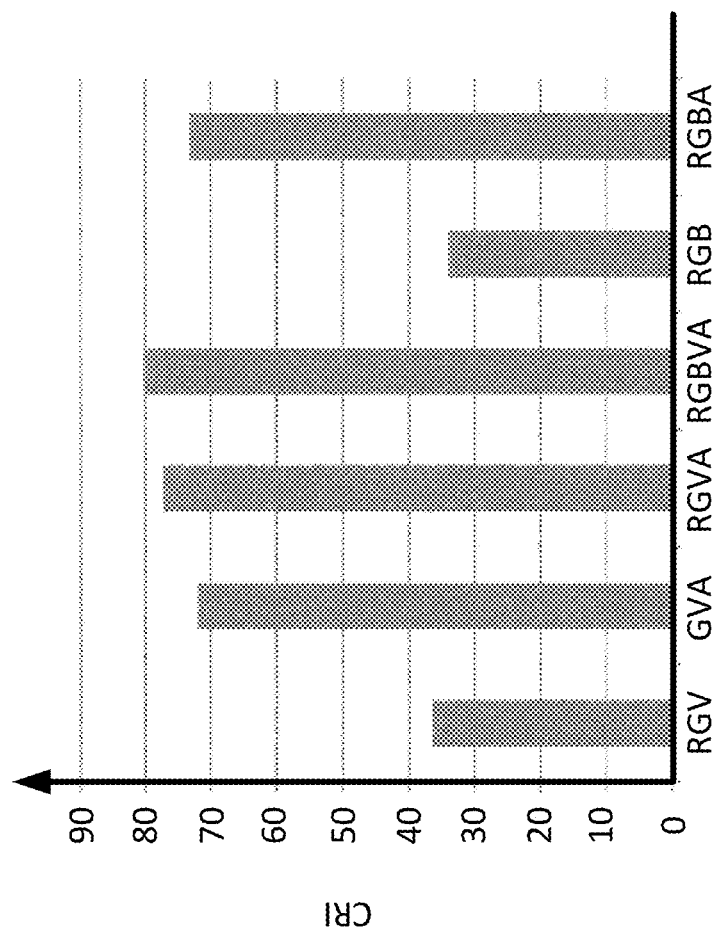
FIG. 3 shows a comparison of measured color rendering index (CRI) values for spectra corresponding to different lighting systems, in accordance with one or more examples disclosed herein.

A CRI corresponding to a lighting system may depend on colors used to implement the system. FIG. 3 shows a comparison of measured CRI values for different lighting systems. Different systems may use multiple colors selected from red (R), green (G), violet (V), amber (A), blue (B), etc. Different diodes may be used for generating different colors. It may be seen that the addition of colors to the spectra may improve the CRI.

In some examples, generating disinfecting white light may comprise combining a first light source emitting in the Soret with another light source that operates on the opposite side of the black body curve as seen on a chromaticity diagram (e.g., a CIE 1931 chromaticity diagram). A color coordinate corresponding to the another source, on the other side of the black body curve may, for example, fall on at any point on a line joining a color coordinate corresponding to the first light source to a point, on the black body curve, corresponding to a target color temperature. The target color temperature of white light in this arrangement may be changed by changing the color coordinate of one of the light sources.

Figure 4:
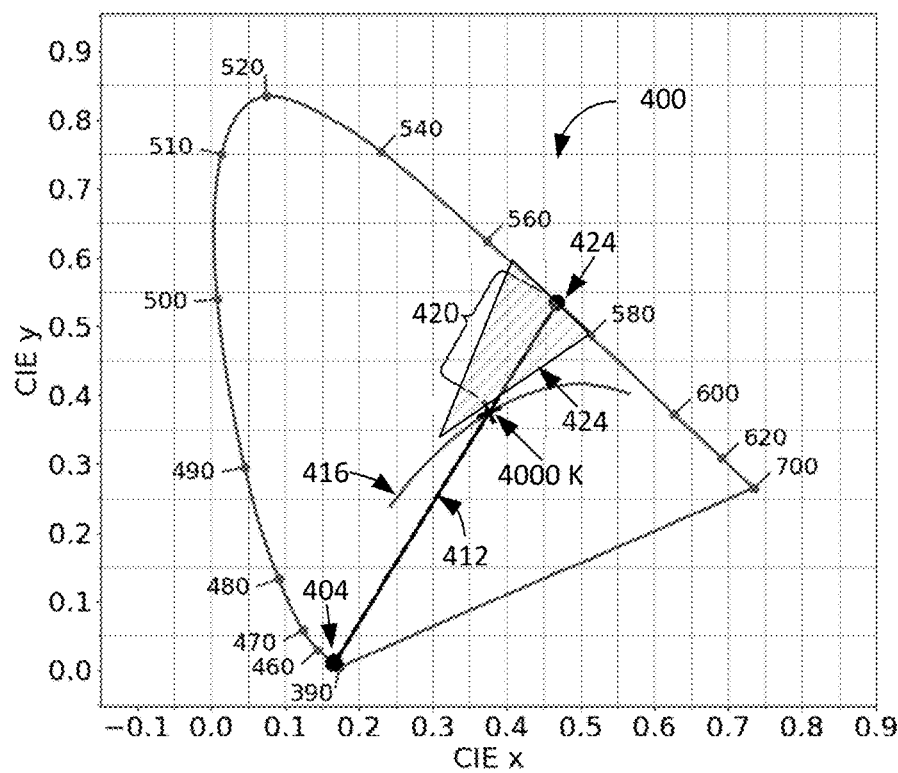
FIG. 4 shows a CIE 1931 chromaticity diagram 400 representing an example technique for generating a disinfecting white light, in accordance with one or more examples disclosed herein.

FIG. 4 shows a CIE 1931 chromaticity diagram 400 representing an example technique for generating a disinfecting white light. A minimal method for generating the white light is to use a first light source emitting light within the Soret band (represented by a color coordinate 404) and directly pairing an additional second light source matched to any point on the other side of the black body curve on the CIE 1931 chromaticity diagram 400. The CIE 1931 chromaticity diagram 400, for example, corresponds to generation of a disinfecting white light with a color temperature of 4000 K. The first light source, for example, may correspond to a 400 nm light source. To generate white light with 4000 K color temperature, the second light source may operate, in a portion 420, of a line 412 connecting the color coordinate 404 to a 4000 K color temperature point on a black body curve 416. The second light source may, for example, operate on the chromaticity curve (e.g., on a color coordinate 424 operating in a Q band region), Through proper control of intensity of the first light source and the second light source (e.g., using computer or microcontroller methods or an analog circuit), a color coordinate corresponding to a combined output of the first and second light sources may fall on or near the black body curve 416 on the CIE 1931 chromaticity diagram 400. Thus, in some examples, the combined output of the first and the second light sources may be perceived as white. The first and the second light sources, in various examples, may also be combined with one or more other light sources for additional desirable characteristics (e.g., a better CRI).

To cause a change in color temperature, the color coordinate for the combined output may be shifted along the black body curve 416, denoting the color temperature. Color temperature may be changed, for example, with a change in diode selection corresponding to one or both of the first and the second light sources causing a shift in the line 412. For modulation of color temperature in this arrangement, it may be advantageous to change the second light source operating on the other side of the black body curve 416. The second light source may be selected to operate at any point in a region 424 based on a desired color temperature. Changing the second light source may be advantageous because a change corresponding to color coordinate shifts of the second light source may have a more noticeable effect on color temperature than the first light source operating in the Soret band. This characteristic may be seen on the CIE chromaticity diagram 400 as wavelengths in the Soret band are very closely packed in the bottom portion of the diagram, yet the Q band region (e.g., in the region 424) has wavelengths that are relatively spread out.

Figure 5:
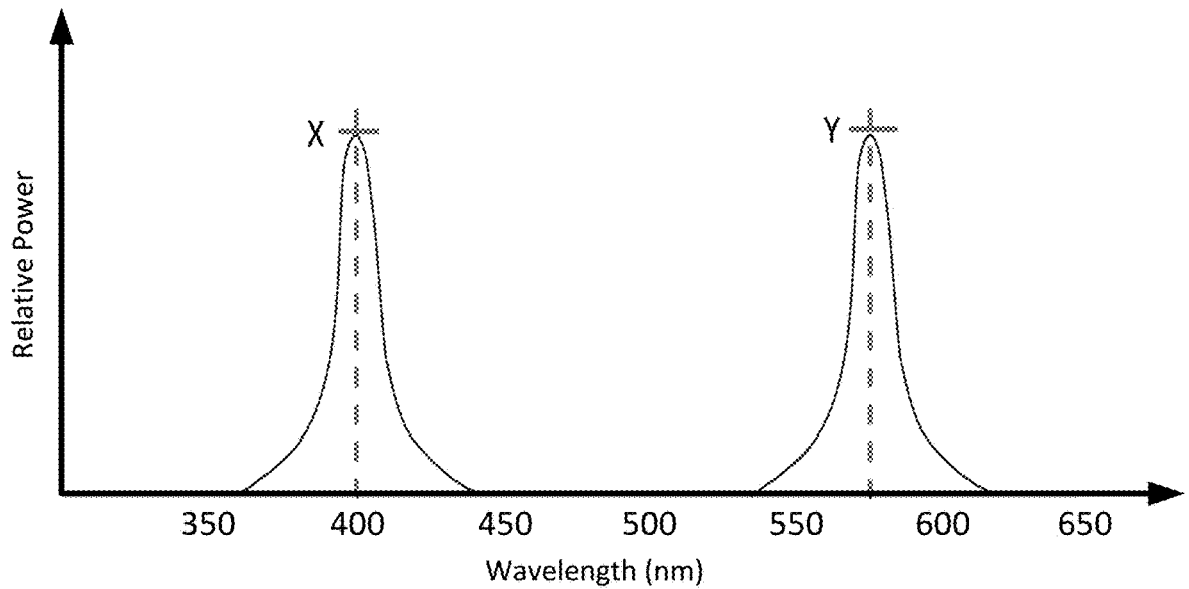
FIG. 5 shows relative power of two light sources as shown in the chromaticity diagram of FIG. 4, in accordance with one or more examples disclosed herein.

In the above arrangement, light emitted by the first and the second light sources may correspond to narrow band emission of wavelengths. The first and the second light sources may be semiconductor-based LEDs that maintain a narrow band emission. Lasers could also be used to narrow the band width (sometimes called full width half max, FWHM). FIG. 5 shows an example of two narrow band light sources X and Y in the Soret band and the Q band region, respectively, being used for generation of disinfecting white light as shown in the chromaticity diagram of FIG. 4. FWHM for each light source is approximated at 10 nm-20 nm with peak heights that are undefined and illustrated as example outputs only.

Figure 6:
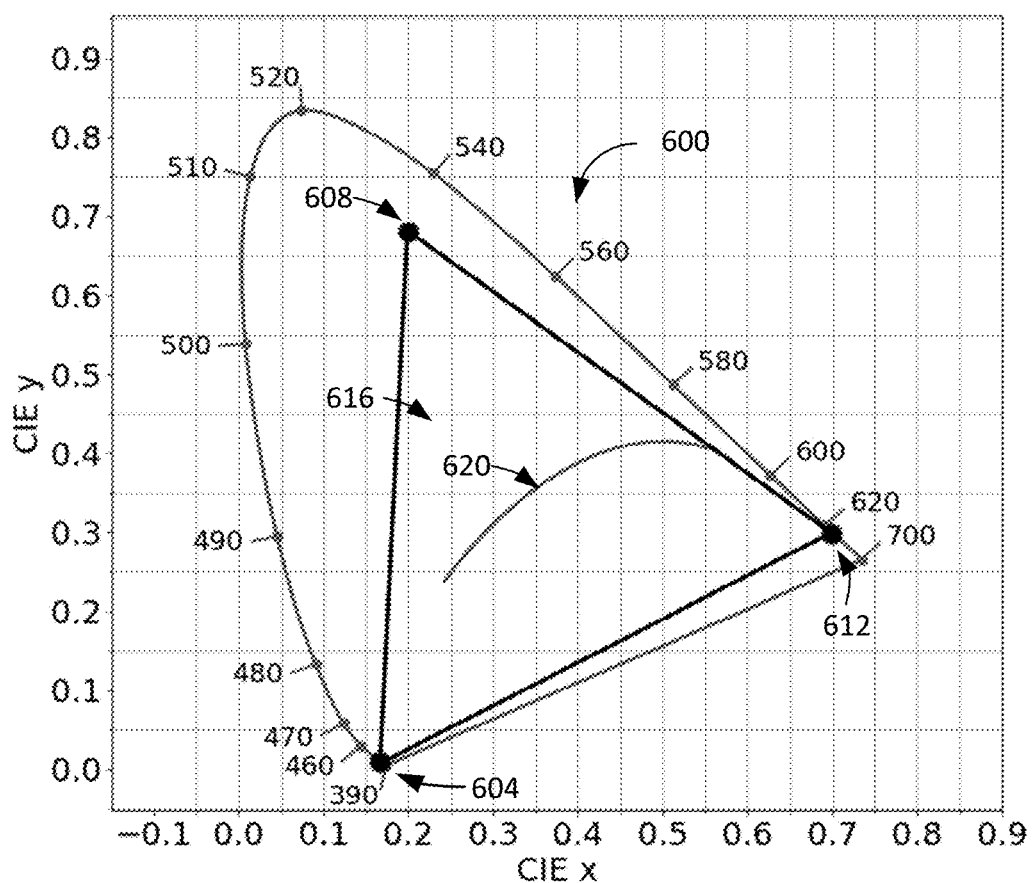
FIG. 6 shows a CIE 1931 chromaticity diagram showing coordinates and the viable combined color coordinate area of red, green, violet mixing, in accordance with one or more examples disclosed herein.

Three light sources may be used, in some examples, for generation of disinfecting light, such as a disinfecting white light or non-white light. Red, green, blue (RGB) color mixing may be used, for example, to generate disinfecting light. In one example, red, green, and violet (RGV) may serve to match the Q band I, Q band II, and the Soret band, respectively, to match peaks and colors. FIG. 6 shows a CIE 1931 chromaticity diagram 600 showing coordinates and the viable combined color coordinate area of red, green, violet mixing for generation of white light or non-white light. A violet color light is represented by a color coordinate 604, a green color light is represented by a color coordinate 608, and a red color light is represented by a color coordinate 612. Any color within the region 616 may be generated by appropriate control (e.g., intensity) of the red, green, and violet color lights. The shape of the region 616 may be changed by changing positions of the color coordinates 604, 608, and 612. A white color (or a hue of white color) may be generated by appropriate control of the red, green, and violet color lights to ensure that a resultant color corresponds to a color coordinate that is on a black body curve 620.

Figure 7:
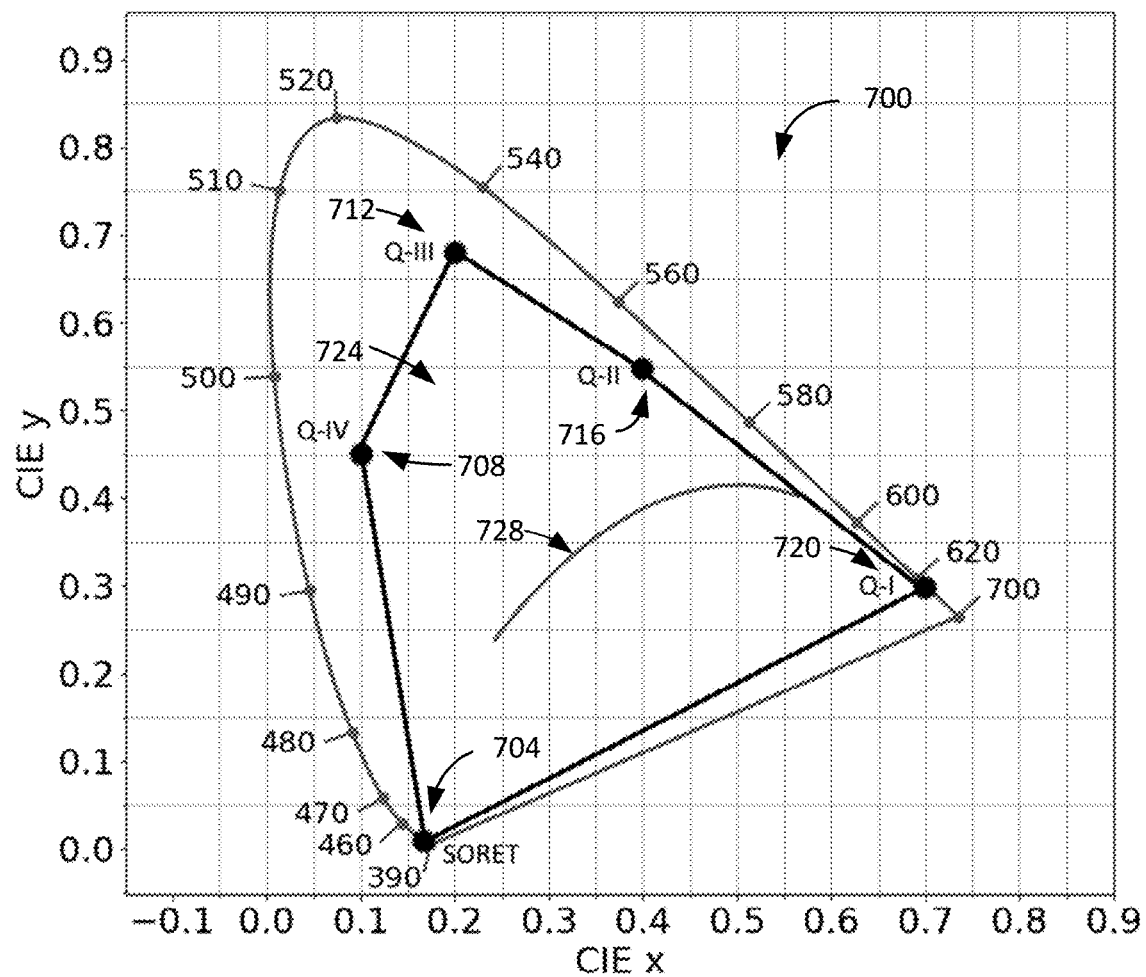
FIG. 7 shows a CIE 1931 chromaticity diagram showing color coordinate layouts of a color mixing situation utilizing a source at the Soret peak, and all Q band peaks, in accordance with one or more examples disclosed herein.

In some examples, it is advantageous to combine a plurality of light sources that are directly matched to each Soret band peak and Q band peak such that, when combined and individually modulated in intensity by a computer or microcontroller source, or an analog circuit, would produce white light or a hue of white. In one example, light sources emitting peaks in the 380 nm-420 nm, 480 nm-520 nm, 510 nm-550 nm, 550 nm-590 nm, and 600 nm-640 nm regions may be combined. FIG. 7 shows a CIE 1931 chromaticity diagram 700 corresponding to generation of white light or non-white light using one or more light sources that are matched to the Soret band and each of the Q band peaks. A Soret band light source is represented by a color coordinate 704, a light source in Q band IV is represented by a color coordinate 708, a light source in Q band III is represented by a color coordinate 712, a light source in Q band II is represented by a color coordinate 716, and a light source in Q band I is represented by a color coordinate 720. Any color within the region 724 may be generated by appropriate control (e.g., intensity) of the light sources operating in the Soret band and the Q band region. Shape of the region 724 may be changed by changing positions of the color coordinates 704, 708, 712, 716, and 720. A white color (or a hue of white color) may be generated by appropriate control of the light sources to ensure that a resultant color corresponds to a color coordinate that is on a black body curve 728. In some examples, all Soret and Q band peaks may be used in a single light source for maximum activation of sensitive peaks.

By combining multiple light sources, the spectrum of the generated white light may be much more complete in the sense that many more wavelengths of light are being emitted at appropriate intensities to provide a higher quality CRI for general illumination. The generated white light may also have a larger color gamut. Using multiple sources may also allow for much greater modulation of color temperature to generate a desired color temperature output. This method may also be used to provide ideal narrow band emissions at each of the peaks (e.g., Soret and Q band peaks).

In examples disclosed herein, it may be advantageous to use commonly available diodes and add a wavelength source in a blue region of light to improve quality of combined light. Diodes in the 380 nm-420 nm region of light may be readily available, but it may be difficult to identify peak matches for other colors. Because a Soret light source (e.g., a Soret match) may be effective in relation to absorption that causes inactivation, it may be advantageous to include a direct light source match across the black body curve from the Soret region to ease factors of color shift. In this case, the Soret match may also serve as an approximate match for the peak of Q band II. For other colors, it is advantageous to use red, green, and/or blue diodes, which are very commonly available. A red diode may be specified to match or approximate to the Q band I peak. A green diode could be specified to match or approximate the Q band III (or Q band IV), and a blue diode could be specified in the 440 nm-480 nm region to improve the quality of the spectrum of light for color rendering. A method that uses a green diode may sacrifice some output for either Q band III or IV peak matches and may serve as an imperfect approximation spectra, but combining the green diode with a violet diode and a blue diode may provide high quality light in terms of color rendering. This method also offers excellent variability in color temperature when tuning of intensities may be completed.

Figure 8:
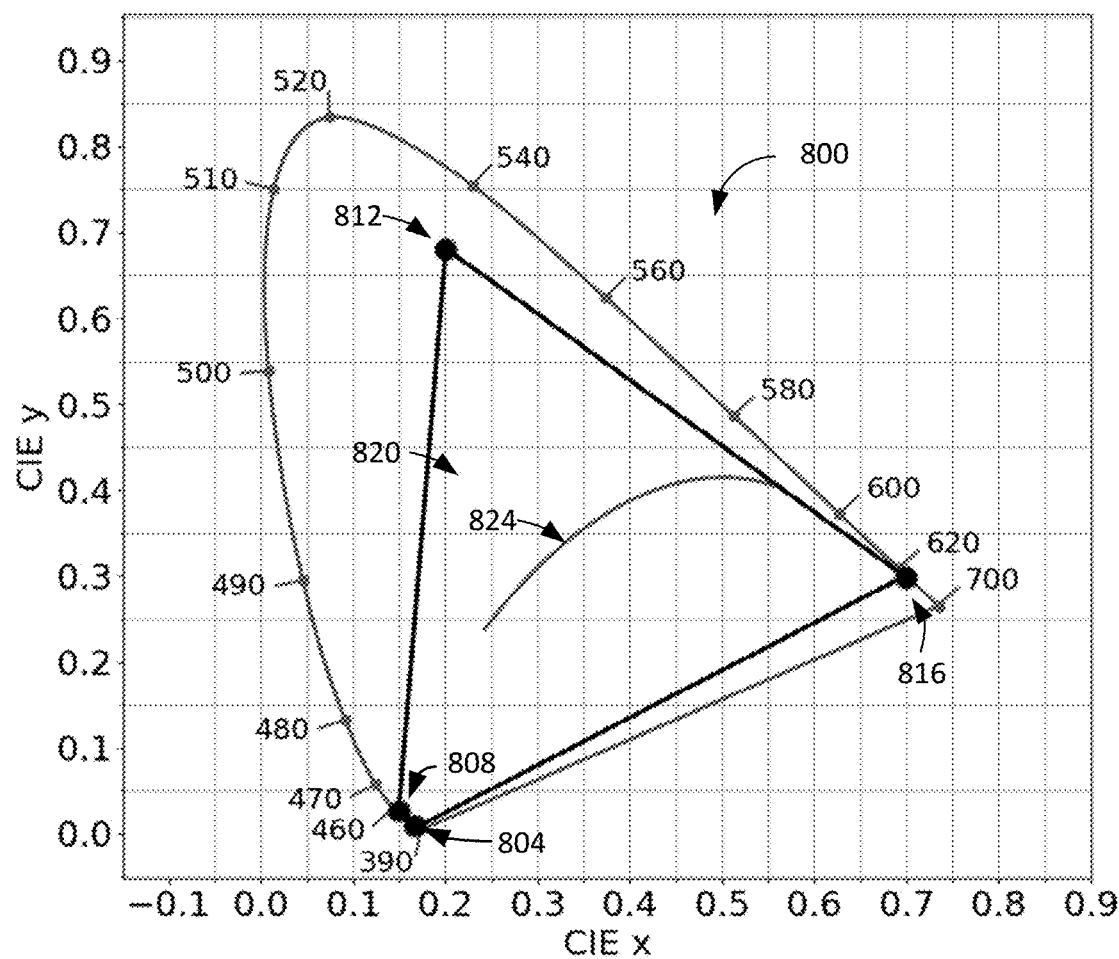
FIG. 8 shows a CIE 1931 chromaticity diagram showing color coordinate layouts of a color mixing situation utilizing a source at the Soret peak, along with red, green, and blue, in accordance with one or more examples disclosed herein.

FIG. 8 shows a CIE 1931 chromaticity diagram 800 corresponding to generation of white light or non-white light using one or more light sources that are matched to the Soret band and the Q band peaks. A Soret band light source is represented by a color coordinate 804, a blue light source is represented by a color coordinate 808, a green light source is represented by a color coordinate 812, and a red light source is represented by a color coordinate 816. Any color within the region 820 may be generated by appropriate control (e.g., intensity) of the Soret band, blue, green, and red light sources. Shape of the region 820 may be changed by changing positions of the color coordinates 804, 808, 812, and 816. A white color (or a hue of white color) may be generated by appropriate control of the light sources to ensure that a resultant color corresponds to a color coordinate that is on a black body curve 824.

In some examples, such as those described in relation to FIGS. 4, 6, 7, and 8, a CRI of generated white light may be increased, along with offering a possibility of modifying the color temperature of the generated white light, by increasing a number of different colors of light being combined to generate the white light. In some examples, such as those described in relation to FIGS. 4, 6, 7, and 8, at least some light sources may correspond to one or more light emitters. The example emitters, in various examples, may emit light corresponding to one or more color coordinates described in FIGS. 4, 6, 7, and 8.

In some examples, the use of phosphor conversion methods in LED devices is advantageous as an effective arrangement in both lighting quality and multiple Soret and Q band activation. Phosphor conversion may comprise generating light through a photochemical absorption/emission. In some examples, a single-light emitting semiconductor source may be used to activate a chemical or combination of chemicals that may be considered a phosphor. The light used to activate the phosphor may be absorbed and emitted from the phosphor at a different wavelength. Phosphor emission may be a broad-band emission in the cyan-red region. This conversion method may be an efficient method for generating light in almost any region of visible light spectrum at efficiencies comparable to semiconductor diodes.

Light-converting materials may comprise a broad category of materials, substances, or structures that have the capability of absorbing a wavelength of light and re-emitting it as another wavelength of light. In some examples, a light-converting material may be a phosphor, an optical brightener, a combination of phosphors, a combination of optical brighteners, or a combination of phosphor(s) and optical brightener(s). In some examples, the light-converting material may be quantum dots, a phosphorescent material, a fluorophore, a fluorescent dye, a conductive polymer, an organometallic phosphor or a combination of any one or more types of light-converting materials.

Light-converting materials, light-converting mediums, light-converting filters, phosphors, and any other terms regarding the conversion of light are meant to be examples of the light-converting material disclosed. A light converting material may be deposited directly on a light source or may be remote or further removed from the light source. Light-converting materials may be deposited, for example, as conformal coatings, doped encapsulants or binder materials, and remote phosphors. In some examples, such as those described in relation to FIGS. 4, 6, 7, and 8, at least some light sources may correspond to one or more light converting materials.

Light-converting layer(s) may comprise multiple light-converting materials and may include any now known or later developed layer(s) for converting all or certain portion(s) of light to different wavelengths. Light-converting layer(s) may tune light to, for example, alter a color tint of exterior surface or the color tint of the material directly surrounding each of light emitters. In any event, the exiting light may be customized to provide disinfection and a desired color.

Because the Soret band is still the largest source of activation in question, an example method comprises using a Soret band light source and a phosphor converted light source as a color match across the black body curve, for white light cases. A color match across the black body curve is not necessarily required for all non-white colors.

Additionally, due to broad band emission of the phosphor conversion method, multiple Q band peaks in the Q band region may be activated by a single light source (e.g., a phosphor converted light source). The broad band emission may also be effective in creating a light spectrum with a high CRI.

In some examples, using a source emitting in the Soret region and a matched phosphor converted diode with appropriate color coordinates, an arrangement may be created that uses only two light sources that may be controlled in their intensity to create a combined output with a color coordinate on the black body curve. The phosphor conversion diode may be powered by a semiconductor chip of any acceptable wavelength as long as the phosphor output matches proper color coordinates. Due to the broad band nature of the phosphor diode, multiple Q band peaks may also be activated.

Different phosphor conversion diodes could be used to cause a matching vector between two light sources to intersect at a desired color temperature on the black body curve. Due to the broad band nature of phosphor, adjustment of color temperature would change intensities matched to each Q band peak, but would not reach a point where no Q band peak would be activated. As Q band peaks may be susceptible to shift due to the organism and the solution they are observed in, it may be desirable to cover the range of the Q band peaks broadly to be able to still have inactivation effectiveness when dealing with Q band peak shifts.

In some examples, it may be desirable to have control of color temperature without changing a phosphor diode. This may be accomplished through the incorporation of red, green, and blue sources in the design. By incorporation of these additional sources, the intensity of all sources could be modulated appropriately by computer or microcontroller methods to cause the color coordinate of the combined output to shift along the black body curve. The red and green diodes used could also be specified to match properly with Q band peaks I and III, respectively, to allow for additional Q band activation.

In some examples, it may be cumbersome and costly to source an exact phosphor diode desired due to readily available supply or upfront engineering costs. An alternative to using an exact phosphor match for the Soret band would be to use commonly available phosphor converted amber diodes.

While a phosphor converted amber diode may not be a direct match for the Soret band as desired, addition of red, green, and blue diodes may offer sufficient modulation of combined output color coordinate through control of intensities using a computer or microcontroller system. The additions of red and green diodes would also allow for additional peak matching with the Q band peaks I and III. While a blue diode may not be required for additional effectiveness in inactivation or the ability to modulate color, it may be desirable, in at least some examples, to include a portion of blue in the spectrum to increase CRI for white light applications.

Some examples use a single light source for generation of inactivating light due to costs and control complexity associated with color mixing and color control in devices that use multiple different light sources. To this end, in some examples, a single component fulfilling the specifications of activating the Soret and at least some Q bands may be used with a phosphor conversion method.

Figure 9A:
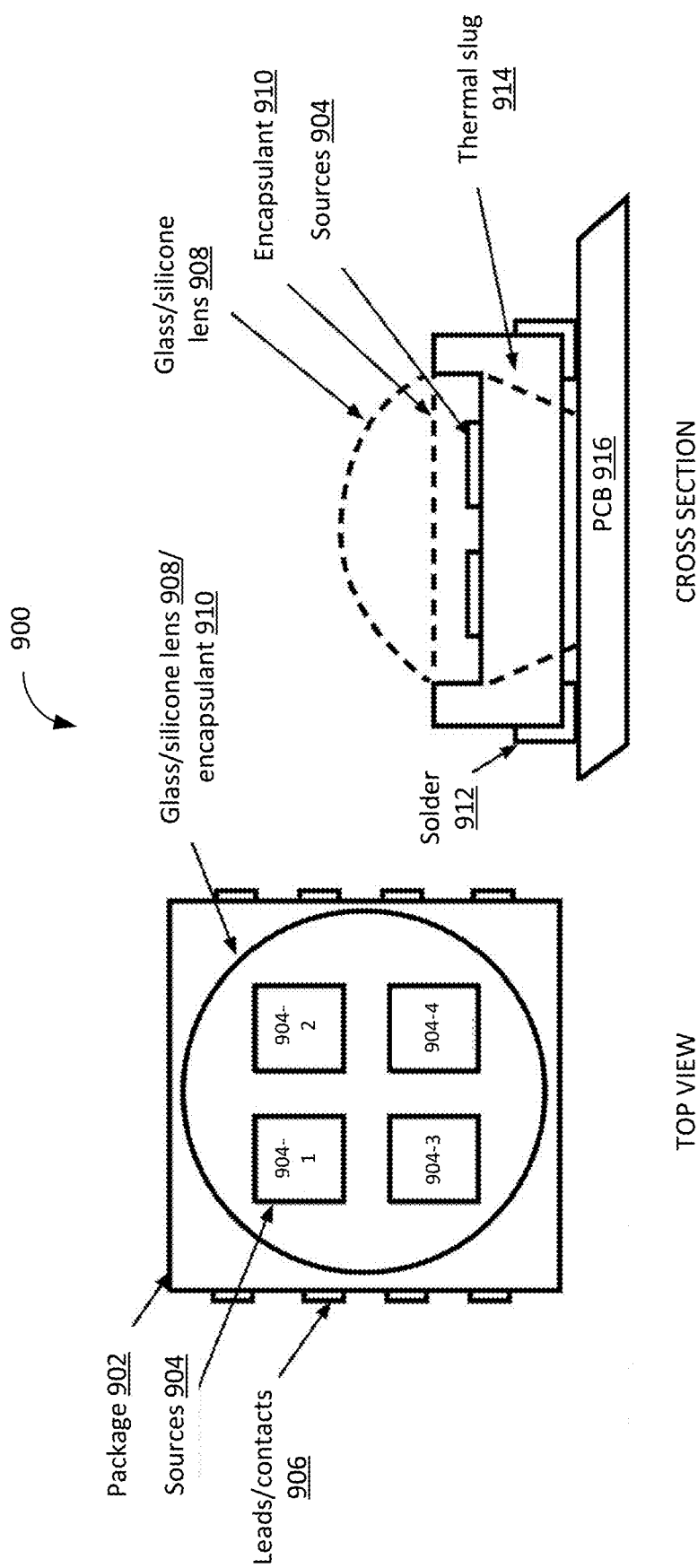
FIGS. 9A-C shows example lighting devices that generate inactivating white light or non-white light, in accordance with one or more examples disclosed herein.

FIG. 9A shows an example lighting device 900 that may generate inactivating white light or non-white light. In some examples, the lighting device 900 may be used to generate light with characteristics as described above (e.g., in FIGS. 4-8). The lighting device 900 may comprise a package 902 with sources 904. The light device 900 may further comprise leads/contacts 906 that are directed to the sources 904 to energize the sources 904. In some examples, a gold wire may be used to connect the leads/contacts 906 to the sources 904. In some examples, the lighting device may further include glass/silicone lens 908, encapsulant 910 over the sources 904, and a thermal slug 914. The thermal slug 1014 may be used to ensure proper heat dissipation from the package 1002. Solder 1012 may be used to ensure proper contact of the package 902 to a PCB 916.

In some examples, the lighting device 900 may produce white light or non-white light with disinfecting wavelengths in both the Soret and Q bands. In some examples, the sources 904 are in a Red, Green, Blue, Violet (RGBV) tunable LED. In some examples, the sources 904 comprise of sources 904-1, 904-2, 904-3 and 904-4. In some examples, source 904-1 is a green source, source 904-2 is a red source, source 904-3 is a phosphor-converted white source, and source 904-4 is a source that emits light in the Soret band (e.g., 380 nm-420 nm). In some examples, power to each of the separate color light sources 904 may be controlled to alter the overall combined output of the lighting device 900. In some examples, the sources 904 may comprise of different LEDs, different light converting materials, and/or respective different light converting materials deposited on one or more LEDs, etc.

Figure 9B:
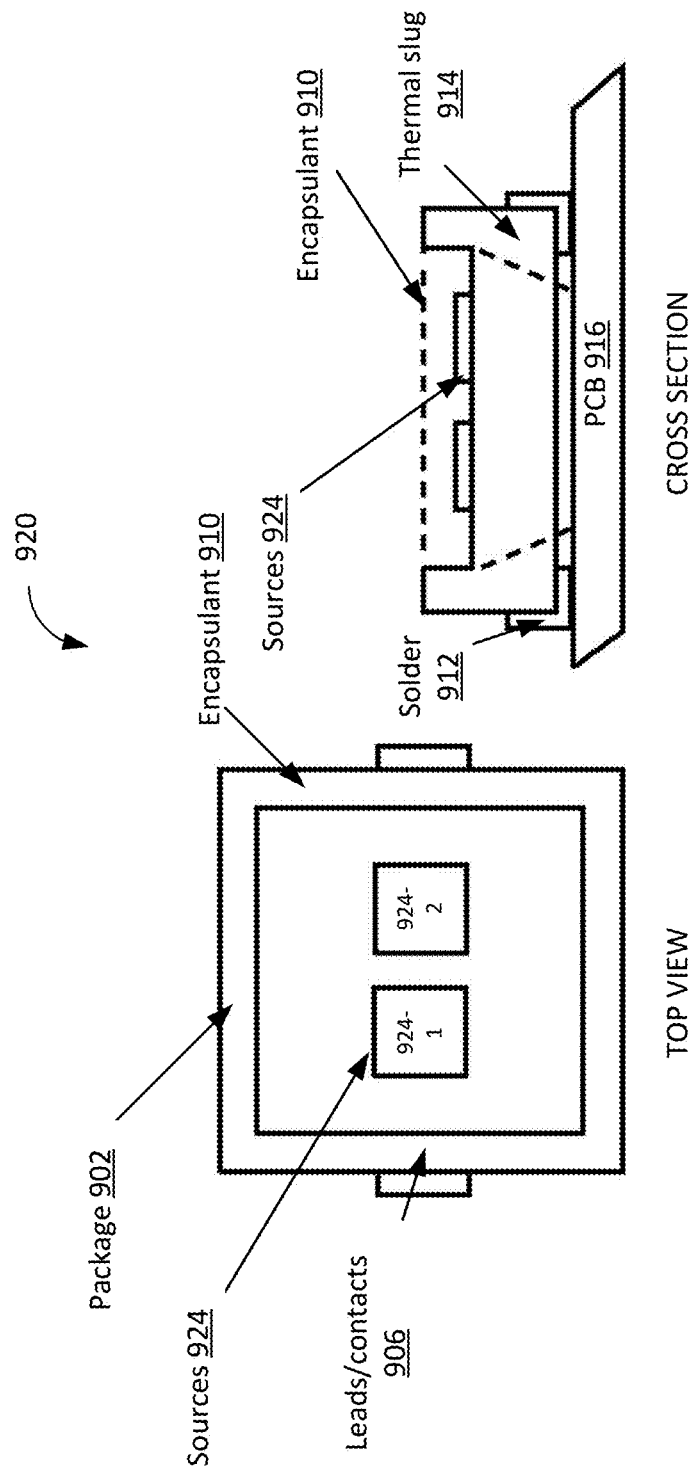

FIG. 9B shows another example lighting device 920 that generates inactivating white light or non-white light. In some examples, the lighting device 920 may be used to generate light with characteristics as described above (e.g., in FIGS. 4-8). In some examples, the lighting device 920 is used to generate light in a manner similar to the lighting device 900. In some examples, the lighting device 920 has components that are similar to those described above in FIG. 9A and like-numbered elements are not discussed in detail for brevity.

The lighting device 920 comprises sources 924. In some examples, the lighting device 924 may comprise of two sources 924-1 and 924-2. In some examples, the source 924-1 may be a source that emits light in the Soret band (e.g., 380 nm-420 nm), and the source 924-2 may be a source that emits light in one or more of the Q bands. In some examples, the sources 924 may comprise of different LEDs, different light converting materials, respective different light converting materials deposited on one or more LEDs, etc.

Figure 9C:
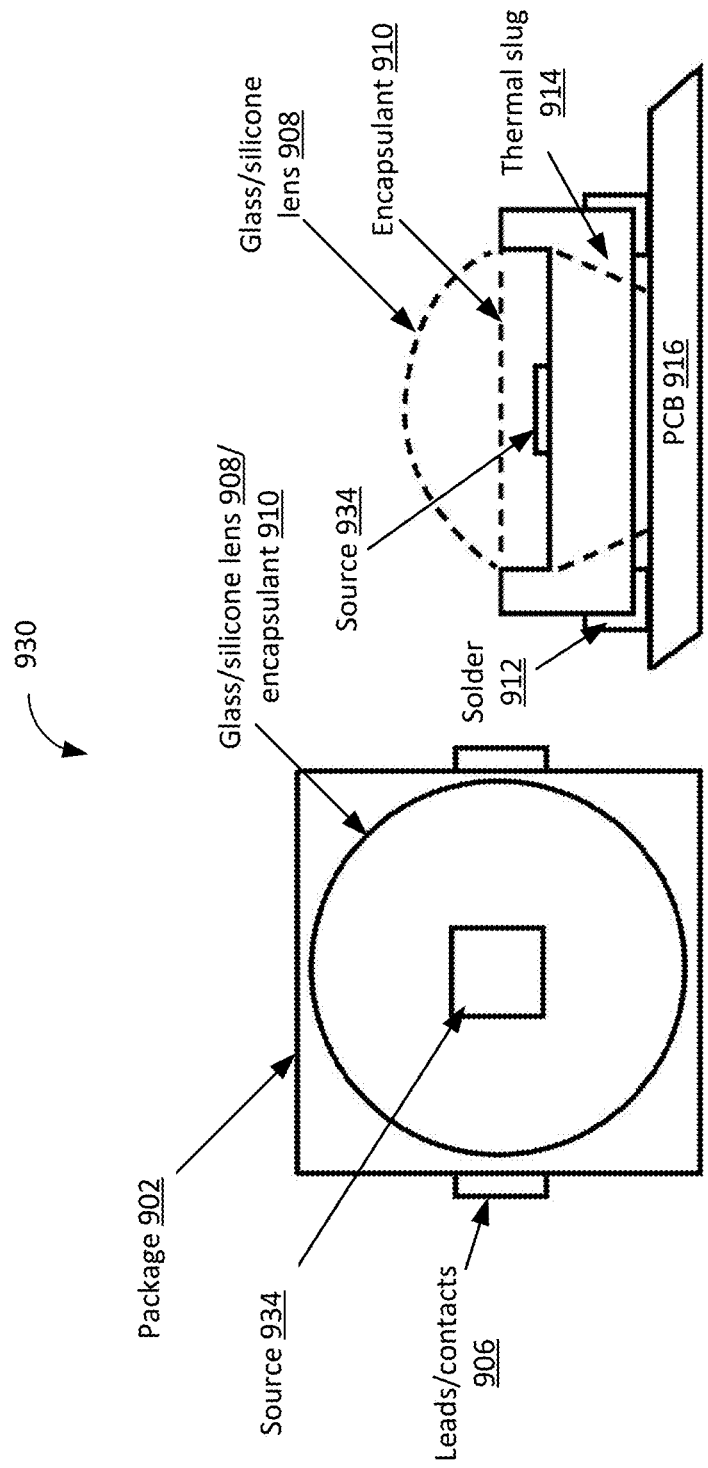

FIG. 9C shows another example lighting device 930 that generates inactivating white light or non-white light. In some examples, the lighting device 930 may be used to generate light with characteristics as described above (e.g., in FIGS. 4-8). In some examples, the lighting device 930 is used to generate light in a manner similar to the lighting device 900. In some examples, the lighting device 930 has components that are similar to those described above in FIG. 9A and like-numbered elements are not discussed in detail for brevity. The lighting device 930 further comprises source 934. In some examples, the source 934 is a source that emits light both in the Soret band (e.g., 380 nm-420 nm) and in one or more of the Q bands.

Phosphor converted diodes may emit just the light from the phosphor emission, or they may be designed to let some of the light from the source activating the phosphor escape the light source and be perceived. In some examples, a single LED component may be a semiconductor chip emitting light in the 380 nm-420 nm region that activates a phosphor encasing or encompassing the semiconductor, or incorporated into the light fixture or device (a method that may be be described as a remote phosphor). In some examples, the source 1034 may comprise of a single emitter that comprises a semiconductor chip (e.g., a diode junction) emitting light in the 380 nm-420 nm region and further comprises a phosphor encasing that is used to absorb light in the 380 nm-420 nm region and emit light in one or more Q bands.

A single non-tunable LED with at least one semiconductor die emitting light within the Soret band 380 nm-420 nm may also be a method for making a non-white multiple band spectrum. This LED may contain at least one light converting material to convert at least a portion of the light from the at least one semiconductor die to a different wavelength. The combined output of the LED forms a non-white color with sufficient energy in the Soret and Q bands to inactivate microorganisms. A single LED package may include one or more semiconductor dies that are each emitters within an LED package. There may be more than one emitter within the LED package, so long as one of them emits a peak wavelength in the range of 380 nm-420 nm.

In some examples, the lighting devices 900, 920, and/or 930 may interface with a control system that allows a minimum intensity of a corresponding wavelength range to be set either by a user or to a predetermined value. A proportion of spectral energy is defined as an amount of spectral energy within a specified wavelength range, e.g., the 380 nm-420 nm wavelength range, divided by a total amount of spectral energy. Proportion of spectral energy is often presented as the spectral energy within the specified wavelength range as a percentage of the total amount of spectral energy.

In some examples, if a minimum proportion of spectral energy of light within the range of 380 nm-420 nm out of a total energy in the 380 nm-750 nm range of visible light, measured as a percentage, is set to be 75%, it may limit a number of colors that may be created but may ensure that disinfecting energy content is high enough to provide a high rate of microbial inactivation. In one specific non-limiting example, minimum energy within the range of 380 nm-420 nm may be set to 40%, which may allow one of possible color options to be a warm hue of white for use at night time or when high quality white light is not needed. In some cases, a maximum proportion of spectral energy of 30% within the range of 380 nm-420 nm is desired to create more white light options. This white light may also be color temperature tunable ranging from 1,000 Kelvin to 6,000 Kelvin, an example of a warm color temperature being 2700K and an example of a cool color temperature being 4100K. These examples are focusing specifically on controlling the proportion of spectral energy in the Soret range, but proportions of spectral energies in other ranges of light (e.g., the Q bands) may also be similarly controlled for various application scenarios.

In some examples, a combined light (e.g., as generated by lighting devices 900, 920, and/or 930) is white and has one or more of the following properties: (a) a correlated color temperature (CCT) value of 1000K to 8000K, (b) a CRI value of 55 to 100, (c) a color fidelity (Rf) value of 60 to 100, and/or (d) a color gamut (Rg) value of 60 to 140.

In one non-limiting example a combined light (e.g., as generated by lighting devices 900, 920, and/or 930) may be white and have a CRI value of at least 70, a CCT between approximately 2,500 K and 5,000 K and/or a proportion of spectral energy measured in the 380 nm to 420 nm wavelength range between 10% and 44%.

There may be a minimum amount of irradiance required in order to disinfect a surface disposed a certain distance away from one or more light sources. For the Soret band wavelength range alone, for example, there may be a minimum irradiance required to hit the surface to cause microbial inactivation. A minimum irradiance of light (e.g., in the 380 nm-420 nm wavelength) on a surface may cause microbial inactivation. For example, a minimum irradiance of 0.02 milliwatts per square centimeter (mW/cm$^2$) may cause microbial inactivation on a surface over time. In some examples, an irradiance of 0.05 mW/cm$^2$ may inactivate microorganisms on a surface, but higher values such as 0.1 mW/cm$^2$, 0.5 mW/cm$^2$, 1 mW/cm$^2$, or 2 mW/cm$^2$ may be used for quicker microorganism inactivation. In some examples, even higher irradiances may be used over shorter periods of time, e.g., 3 to 10 mW/cm$^2$.

For the Soret band wavelength range, in some examples, light for microbial inactivation may include radiometric energy sufficient to inactive at least one bacterial population, or in some examples, a plurality of bacterial populations. One or more light sources may have some minimum amount of radiometric energy (e.g., 20 mW) measured in the 380 nm-420 nm wavelength range.

Dosage (measured in Joules/cm$^2$) may be another metric for determining an appropriate irradiance for microbial inactivation over a period of time. Table 1 below shows example correlations between irradiance in mW/cm$^2$ and Joules/cm$^2$ based on different exposure times for the Soret band. These values are examples and many others may be possible.

TABLE 1

| Irradiance (mW/cm$^2$) | Exposure Time (hours) | Dosage (Joules/cm$^2$) |
|---|---|---|
| 0.02 | 1 | 0.072 |
| 0.02 | 24 | 1.728 |
| 0.02 | 250 | 18 |
| 0.02 | 500 | 36 |
| 0.02 | 1000 | 72 |
| 0.05 | 1 | 0.18 |
| 0.05 | 24 | 4.32 |
| 0.05 | 250 | 45 |
| 0.05 | 500 | 90 |
| 0.05 | 1000 | 180 |
| 0.1 | 1 | 0.36 |
| 0.1 | 24 | 8.64 |
| 0.1 | 250 | 90 |
| 0.1 | 500 | 180 |
| 0.1 | 1000 | 360 |
| 0.5 | 1 | 1.8 |
| 0.5 | 24 | 43.2 |
| 0.5 | 250 | 450 |
| 0.5 | 500 | 900 |
| 0.5 | 1000 | 1800 |
| 1 | 1 | 3.6 |
| 1 | 24 | 86.4 |
| 1 | 250 | 900 |
| 1 | 500 | 1800 |
| 1 | 1000 | 3600 |

Table 2 shows the different dosages recommended for the inactivation of different bacterial species using narrow spectrum 405 nm light. Inactivation is not limited to these bacteria. Recommended dosage is measured by a dosage required for a 1-Log reduction in bacteria.

TABLE 2

| Organism | Recommended Dose (J/cm$^2$) for 1-Log Reduction in Bacteria |
|---|---|
| Staphylococcus aureus | 20 |
| MRSA | 20 |
| Pseudomonas aeruginosa | 45 |
| Escherichia coli | 80 |
| Enterococcus faecalis | 90 |

Equation 1 may be used in order to determine irradiance, dosage, or time using one or more data points from Table 1 and Table 2:

$$\frac{\text{Irradiance}\left(\frac{mW}{cm^2}\right)}{1000} * \text{Time(s)} = \text{Dosage}\left(\frac{J}{cm^2}\right) \quad \text{Equation 1}$$

Irradiance may be determined based on dosage and time. For example, if a dosage of 30 Joules/cm$^2$ is required and the object desired to be disinfected is exposed to light overnight for 8 hours, the irradiance may be approximately 1 mW/cm$^2$. If a dosage of 50 Joules/cm$^2$ is required and the object desired to be disinfected is exposed to light for 48 hours, a smaller irradiance of only approximately 0.3 mW/cm$^2$ may be sufficient. These calculations are done assuming the use of light in the Soret band range of 380 nm-420 nm.

Time may be determined based on irradiance and dosage. In some examples, a device may be configured to emit an irradiance of disinfecting energy (e.g., 0.05 mW/cm$^2$) and a target bacteria may require a dosage of 20 Joules/cm$^2$ to kill the target bacteria. Disinfecting light at 0.05 mW/cm$^2$ may have a minimum exposure time of approximately 4.6 days to achieve the dosage of 20 Joules/cm$^2$. Dosage values may be determined by a target reduction in bacteria. Once the bacteria count is reduced to a desired amount, disinfecting light may be continuously applied to keep the bacteria counts down. These calculations are done assuming the use of light in the Soret band range of 380 nm-420 nm.

Table 3 shows one interpretation of the different disinfecting ranges of light including the Soret band and four Q bands. Different porphyrins have different peak absorption wavelengths within each of the ranges which emphasizes the need for wide band light sources.

TABLE 3

| | |
|---|---|
| Soret | 400-435 nm |
| Q IV | 497-526 nm |
| Q III | 532-563.5 nm |
| Q II | 566-595 nm |
| Q I | 593-650.5 nm |

In various examples, an approximate ratio may be used to compare portions of different wavelength ranges within a spectrum of light. In one specific non-limiting example corresponding to white light, there may be a 3:1:1 ratio of spectral energy measured within wavelength ranges 380 nm-420 nm, 490 nm-530 nm, and 530 nm-660 nm, respectively, wherein the minimum irradiance of the 380 nm-420 nm range is at least 0.02 mW/cm$^2$.

In some examples for white light, a proportion of spectral energy, in total spectral energy of a light source, within the Soret band wavelength range of 380 nm-420 nm is at least 20% and a remaining proportion of spectral energy is within the Q Band range of 490 nm-660 nm. In some examples, there may be one peak wavelength within the 380 nm-420 nm range and one or more peak wavelengths within the 490 nm-660 nm range. In some examples, a minimum irradiance within the range of 380 nm-420 nm is 0.02 mW/cm$^2$. In some examples, there may be an additional peak within a wavelength range of 440 nm-480 nm to improve color rendering. In some examples, a proportion of spectral energy within a wavelength range 440 nm-480 nm is less than 15%.

In various examples for non-white light, an approximate ratio may be used to compare portions of different wavelength ranges within a spectrum of the non-white light. In some examples, there may be a 1:3:3 ratio of spectral energy measured within wavelength ranges of 380 nm-420 nm, 490 nm-530 nm, and 530 nm-660 nm, respectively, wherein a minimum irradiance of the 380 nm-420 nm range is at least 0.02 mW/cm$^2$. In this example scenario, the light may be perceived as a bright blue-green color.

Figure 10A:
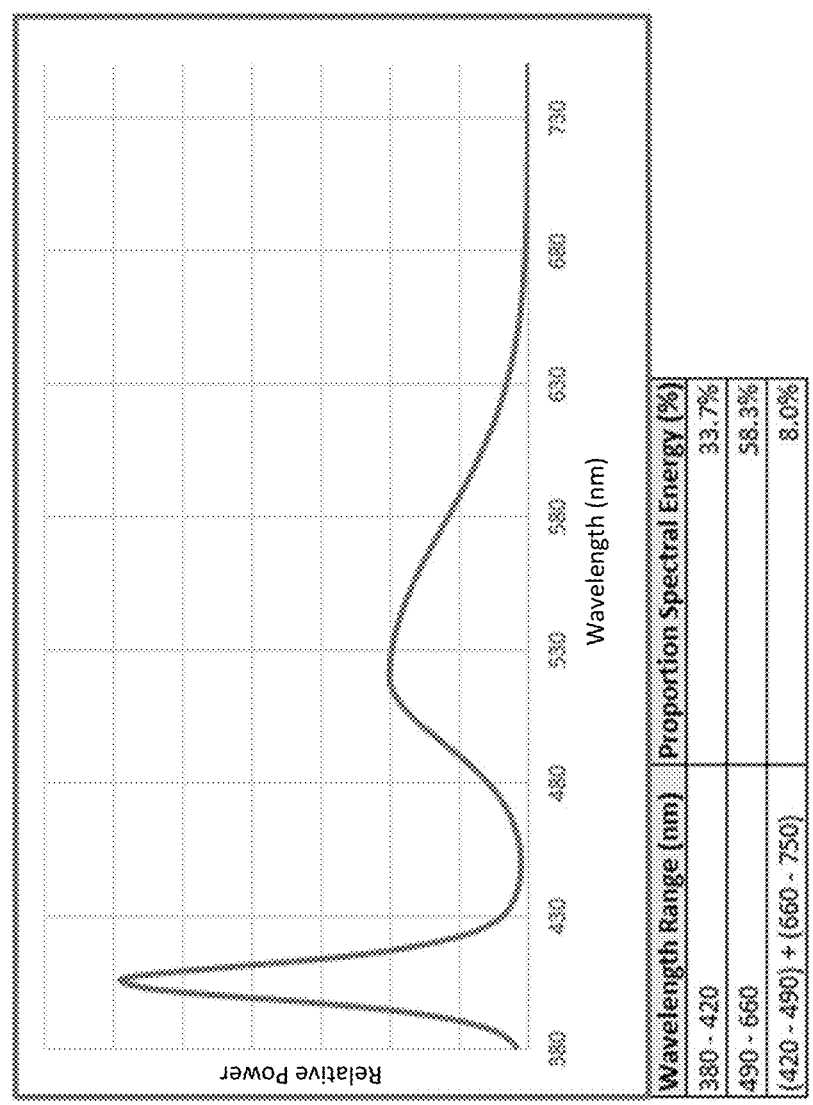
FIG. 10A shows an example spectrum of non-white light and corresponding relative power within specified wavelength ranges, in accordance with one or more examples disclosed herein.
Figure 10B:
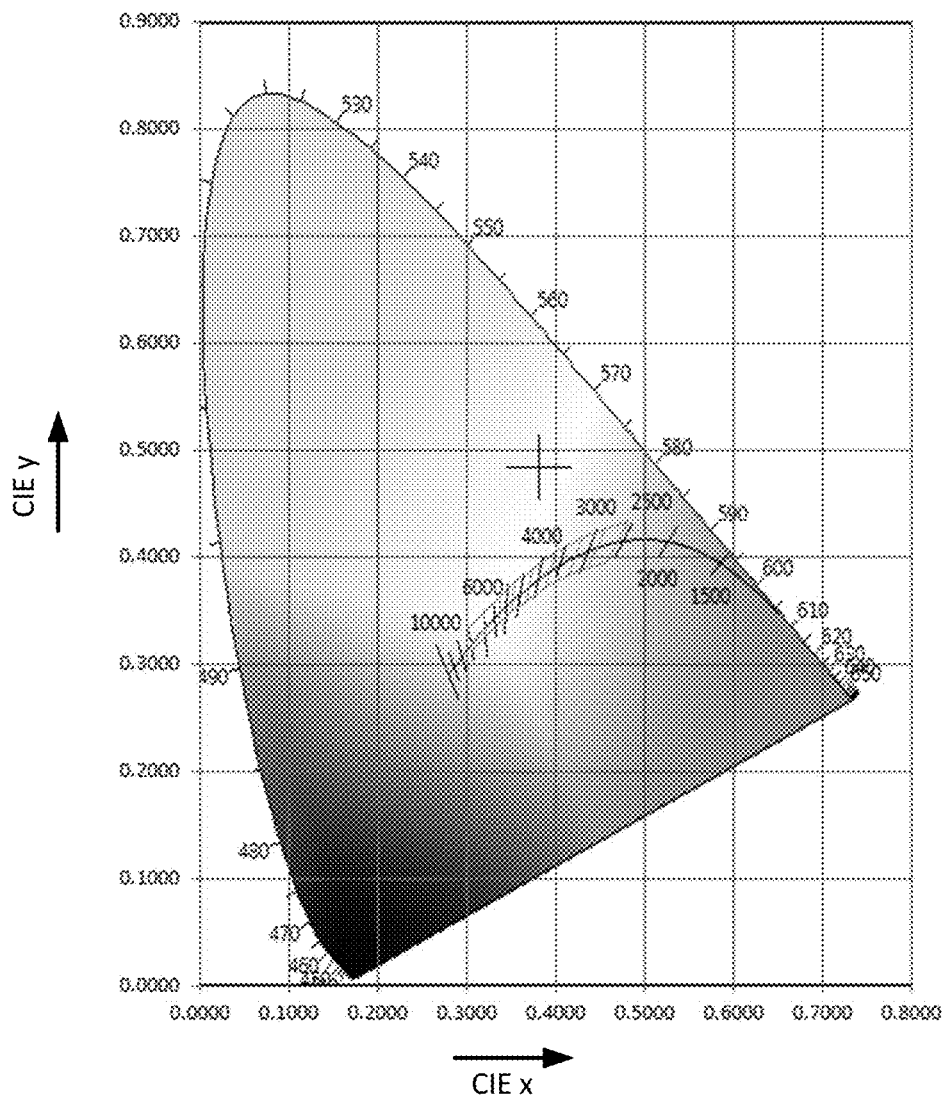
FIG. 10B shows color coordinates corresponding to the spectrum of FIG. 11A graphed on a CIE 1931 chromaticity diagram, in accordance with one or more examples disclosed herein.

FIG. 10A shows an example non-white light emission with an approximate ratio of a peak wavelength at 405 nm to a peak wavelength at 520 nm of 3:1. In an example, the non-white light in FIG. 10A may be perceived as a shade of green. FIG. 10A also shows relative power for the Soret band wavelength range of 380 nm-420 nm, the Q bands range of 490 nm-660 nm, and remaining wavelengths outside those ranges and within 380 nm-750 nm (e.g., 420 nm-490 nm and 660 nm-750 nm). FIG. 10B shows coordinates corresponding to this spectrum graphed onto a chromaticity diagram. A plus sign indicates the location of the coordinates.

Figure 11A:
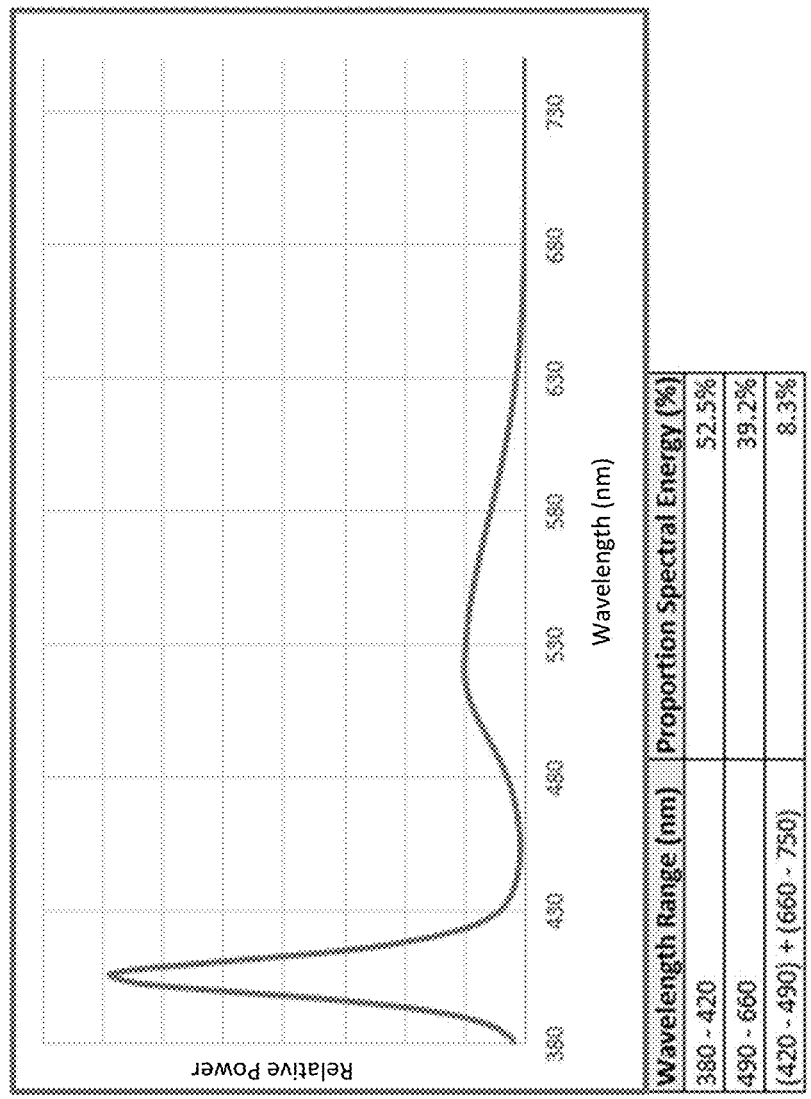
FIG. 11A shows an example spectrum of non-white light and corresponding relative power within specified wavelength ranges, in accordance with one or more examples disclosed herein.
Figure 11B:
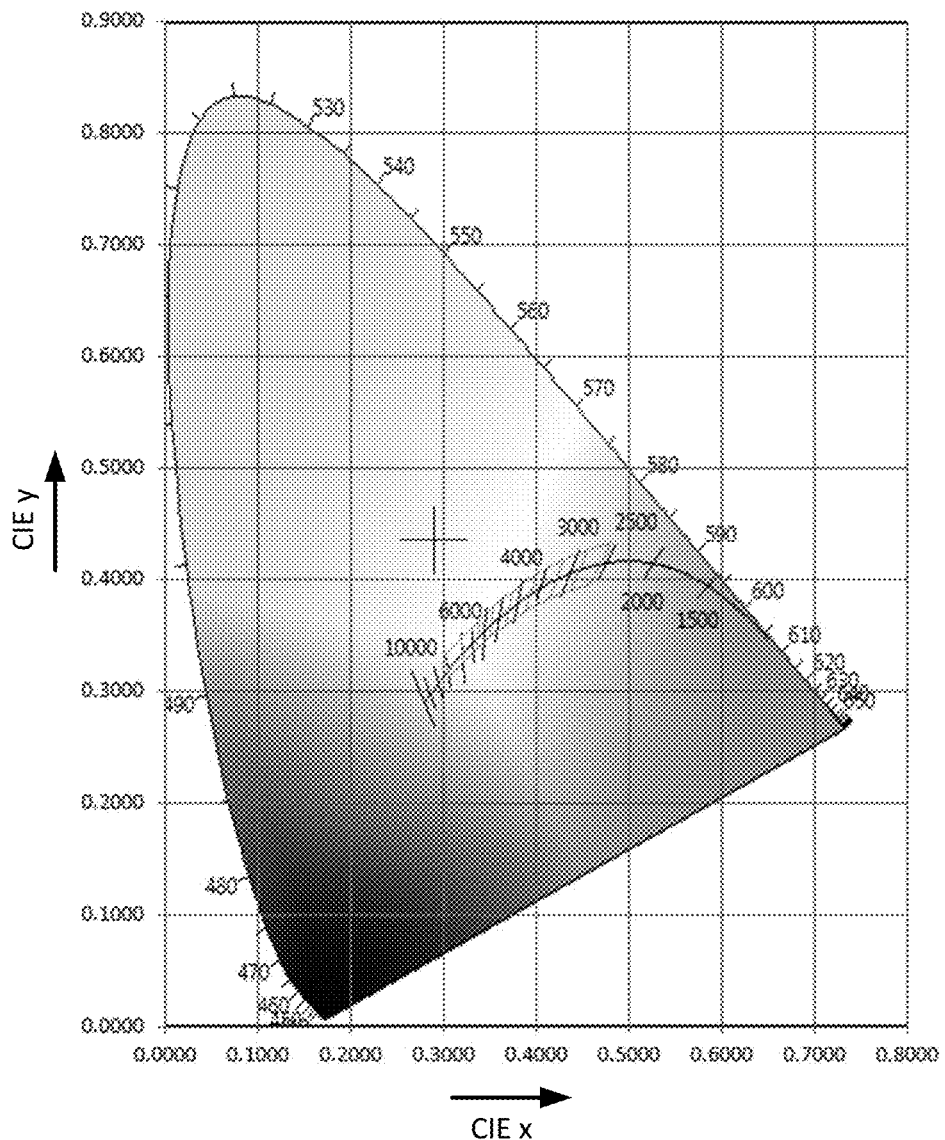
FIG. 11B shows color coordinates corresponding to the spectrum of FIG. 12A graphed on a CIE 1931 chromaticity diagram, in accordance with one or more examples disclosed herein.

FIG. 11A shows an example non-white light emission with an approximate ratio of a peak wavelength at 405 nm to a peak wavelength at 520 nm of 7:1. In some examples, the non-white light in FIG. 11A may be perceived as a shade of green-blue. FIG. 11A also shows relative power for the Soret band wavelength range of 380 nm-420 nm, the Q bands range of 490 nm-660 nm, and remaining wavelengths outside those ranges and within 380 nm-750 nm (e.g., 420 nm-490 nm and 660 nm-750 nm). FIG. 11B shows coordinates corresponding to this spectrum graphed onto a chromaticity diagram. A plus sign indicates the location of the coordinates.

Figure 12A:
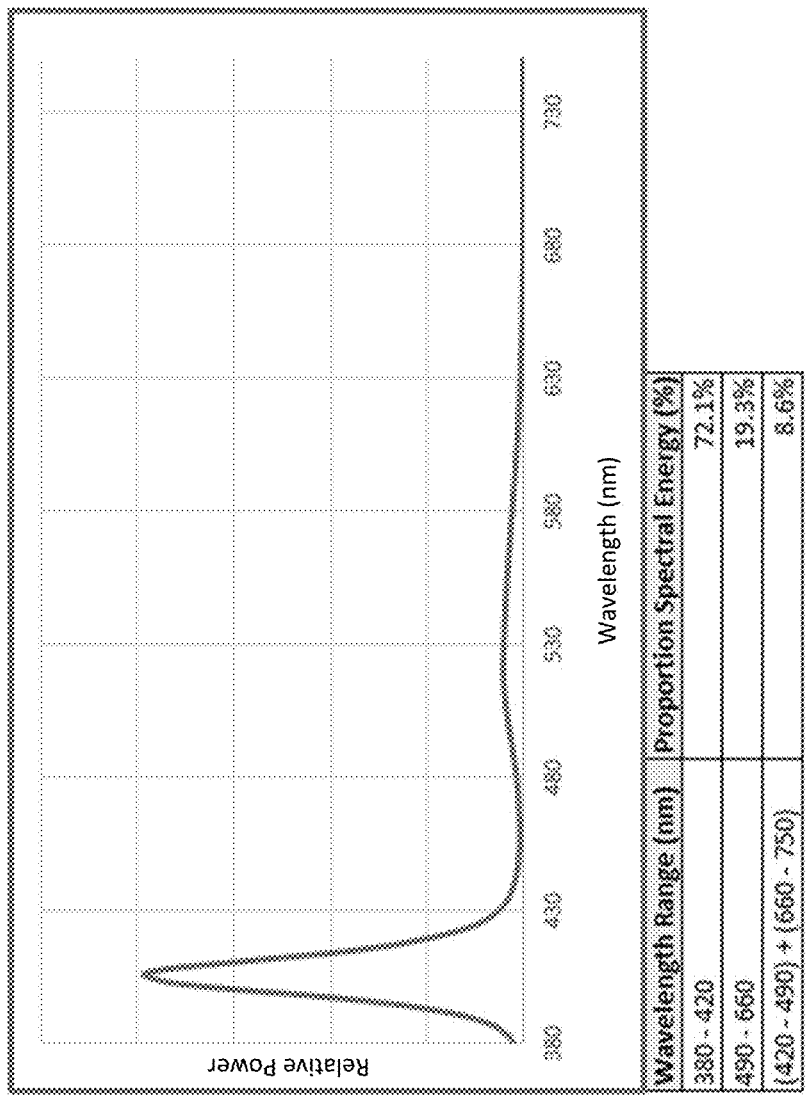
FIG. 12A shows an example spectrum of non-white light and corresponding relative power within specified wavelength ranges, in accordance with one or more examples disclosed herein.
Figure 12B:
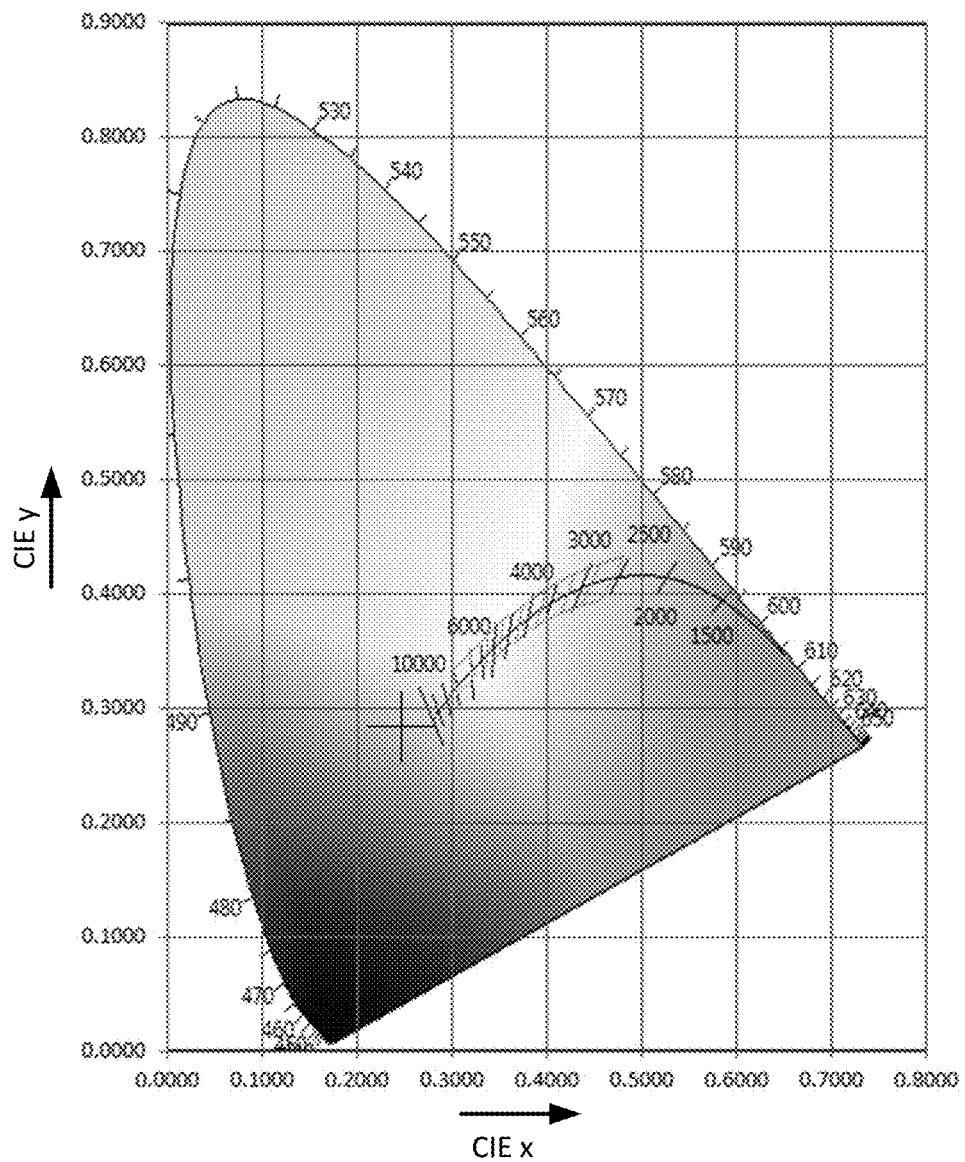
FIG. 12B shows color coordinates corresponding to the spectrum of FIG. 13A graphed on a CIE 1931 chromaticity diagram, in accordance with one or more examples disclosed herein.

FIG. 12A shows an example non-white light emission with an approximate ratio of a peak wavelength at 405 nm to a peak wavelength at 520 nm of 20:1. In some examples, the non-white light in FIG. 12A may be perceived as a shade of blue-violet. FIG. 12A also shows relative power for the Soret band wavelength range of 380 nm-420 nm, the Q bands range of 490 nm-660 nm, and the remaining wavelengths outside those ranges and within 380 nm-750 nm (e.g., 420 nm-490 nm and 660 nm-750 nm). FIG. 12B shows coordinates corresponding to this spectrum graphed onto a chromaticity diagram. A plus sign indicates the location of the coordinates.

Figure 13A:
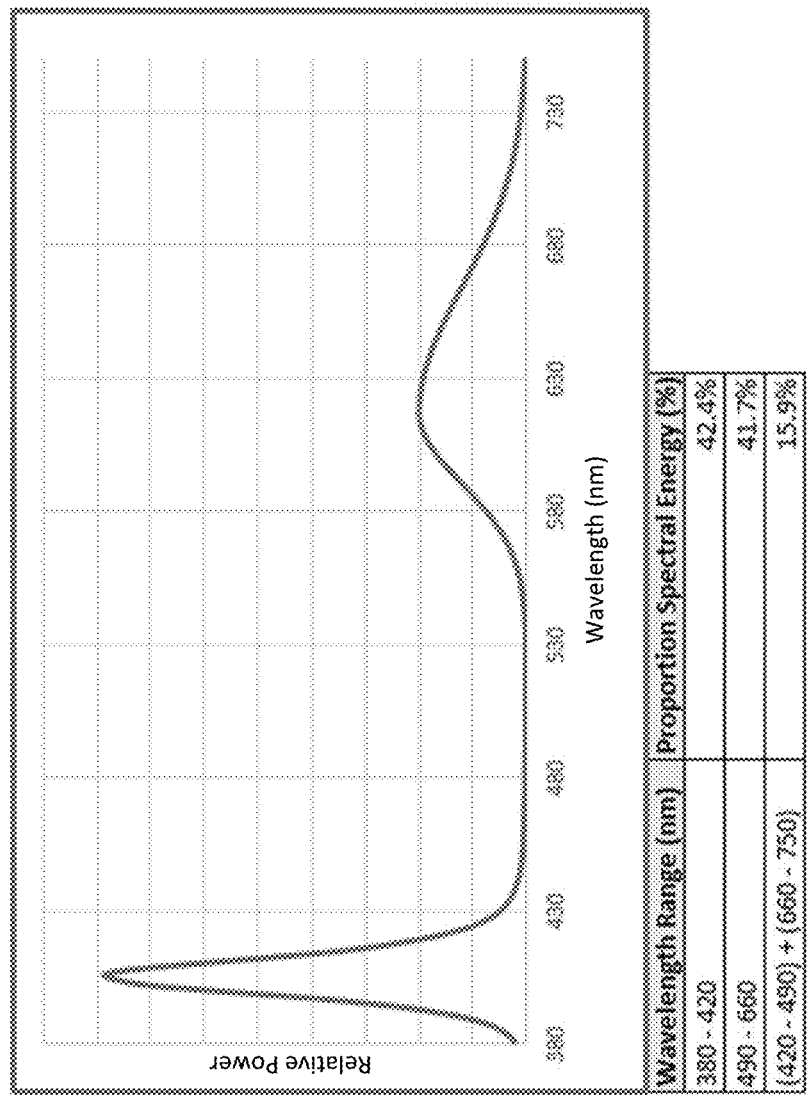
FIG. 13A shows an example spectrum of non-white light and corresponding relative power within specified wavelength ranges, in accordance with one or more examples disclosed herein.
Figure 13B:
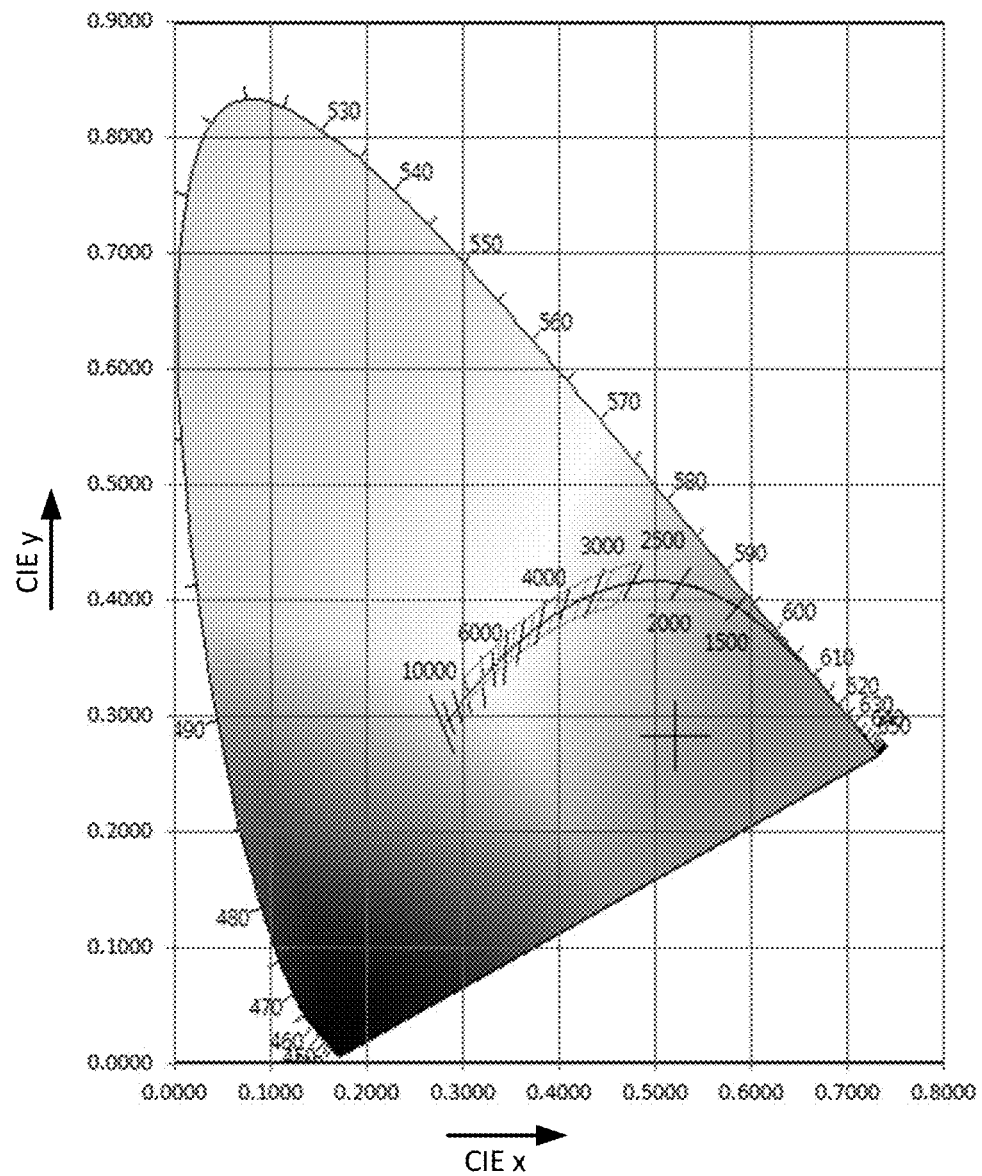
FIG. 13B shows color coordinates corresponding to the spectrum of FIG. 14A graphed on a CIE 1931 chromaticity diagram, in accordance with one or more examples disclosed herein.

FIG. 13A shows an example non-white light emission with an approximate ratio of a peak wavelength at 405 nm to a peak wavelength at 620 nm of 4:1. In some examples, the non-white light in FIG. 13A may be being perceived as a shade of pink. FIG. 13A also shows relative power for the Soret band wavelength range of 380 nm-420 nm, the Q bands range of 490 nm-660 nm, and the remaining wavelengths outside those ranges and within 380 nm-750 nm (e.g., 420 nm-490 nm and 660 nm-750 nm). FIG. 13B shows coordinates corresponding to this spectrum graphed onto a chromaticity diagram. A plus sign indicates the location of the coordinates.

Figure 14A:
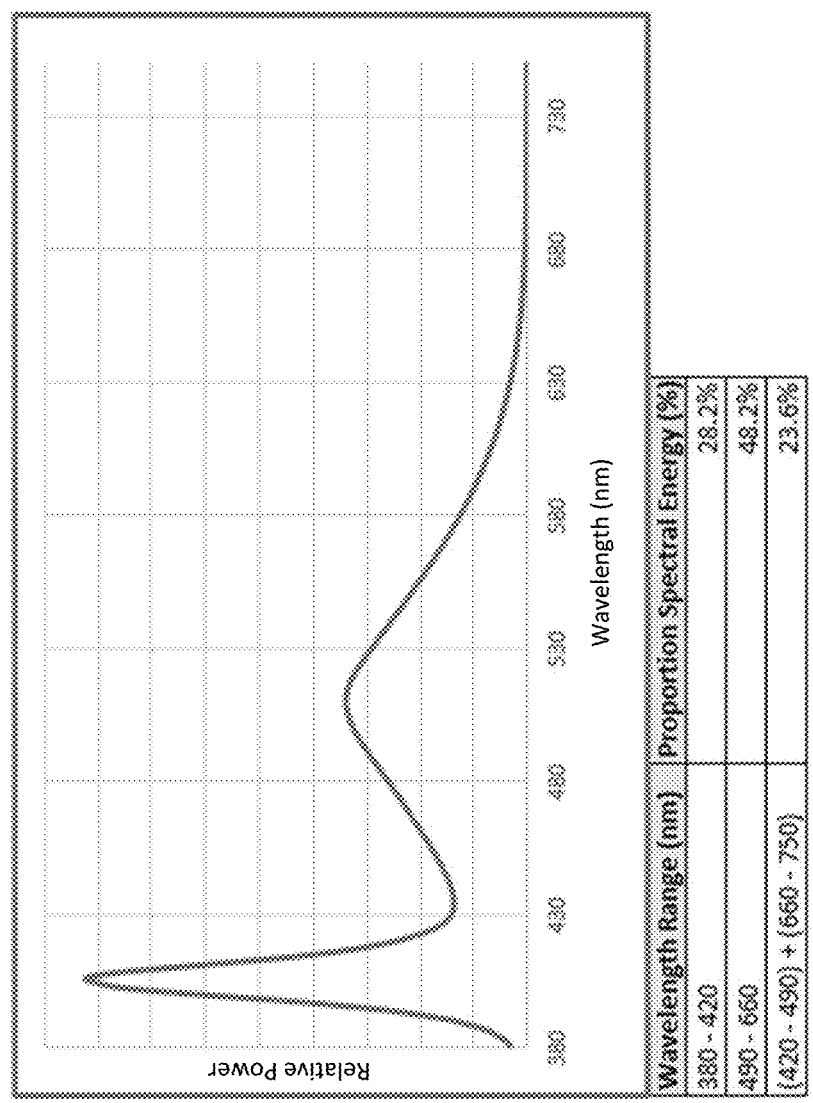
FIG. 14A shows an example spectrum of non-white light and corresponding relative power within specified wavelength ranges, in accordance with one or more examples disclosed herein.
Figure 14B:
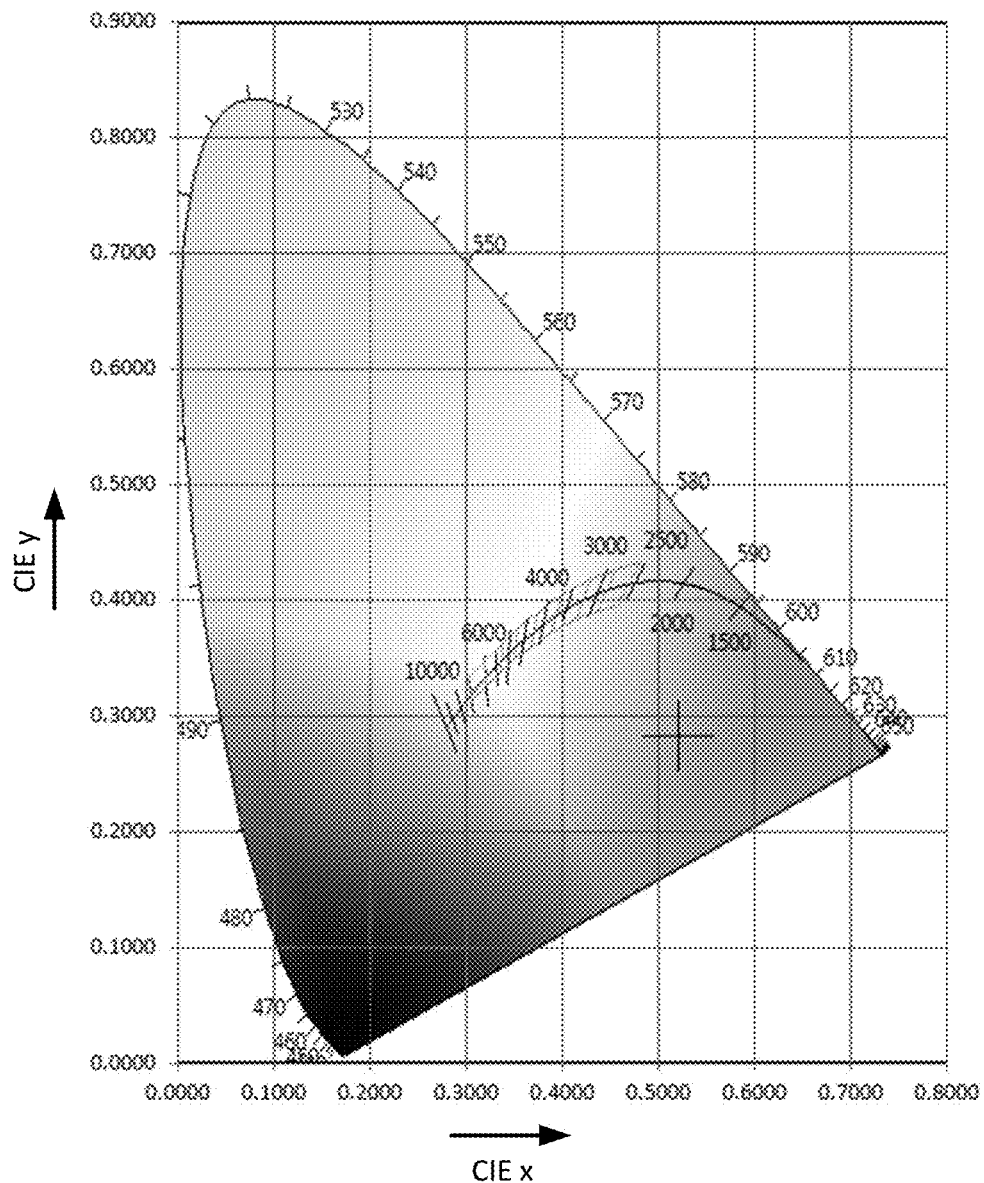
FIG. 14B shows color coordinates corresponding to the spectrum of FIG. 15A graphed on a CIE 1931 chromaticity diagram, in accordance with one or more examples disclosed herein.

FIG. 14A shows an example non-white light emission with an approximate ratio of a peak wavelength at 405 nm to a peak wavelength at 480 nm to a peak wavelength at 520 nm of 4:1:1. In some examples, the non-white light in FIG. 14A may be perceived as a shade of teal. FIG. 14A also shows relative power for the Soret band wavelength range of 380 nm-420 nm, the Q bands range of 490 nm-660 nm, and the remaining wavelengths outside those ranges and within 380 nm-750 nm (e.g., 420 nm-490 nm and 660 nm-750 nm). FIG. 14B shows coordinates corresponding to this spectrum graphed onto a chromaticity diagram. A plus sign indicates the location of the coordinates.

In some examples, non-white light corresponds to a 5:1:1 ratio of spectral energy measured within wavelength ranges 380 nm-420 nm, 490 nm-530 nm, and 530 nm-660 nm, respectively, wherein a minimum irradiance of the wavelength range in the 380 nm-420 nm range is at least 0.02 mW/cm$^2$. In this example scenario, the light may be perceived as a violet color.

In some examples, a highest proportion of spectral energy from a total spectral energy of the light source is within the Soret band wavelength range of 380 nm-420 nm (e.g., 70%), and a remaining proportion of the spectral energy is within the Q band range of 490 nm-660 nm. In some examples, there may be one peak wavelength within the 380 nm-420 nm range and one or more peak wavelengths within the 490 nm-660 nm range. In some examples, a minimum irradiance within the range of 380 nm-420 nm is 0.02 mW/cm$^2$.

Various examples of white light or non-white light as described above may be generated using a lighting device, such the lighting device 900, the lighting device 920, or the lighting device 930. Various examples of white light or non-white light as described above may be generated using a combination of lighting devices, such as two or more of the lighting devices 900, 920, or 930.

Table 4 provides example of non-white color spectrums that may be created using methods, devices, and/or systems disclosed herein. In some examples, a 405 nm pump LED is used in conjunction with one or more phosphors. The phosphors are described by their peak wavelength (Wp) and FWHM value. The ratio column is the ratio of radiometric energy emitted by the 405 nm pump LED to radiometric energy emitted by phosphor 1 to radiometric energy emitted by phosphor 2 (where applicable). Violet % is defined as the percentage of energy in the range of 380 nm-420 nm out of total energy emitted. The RGB Color is a set of 8-bit color values from the RGB color space that represent a color, encoded in the order of: Red, Green, Blue.

TABLE 4

| Phosphor 1 | Phosphor 2 | Ratio | Violet % | RGB Color |
|---|---|---|---|---|
| Wp: 543 nm, FWHM 54 nm | Wp: 612 nm, FWHM 75 nm | 100:10:10 | 76 | 214, 165, 255 |
| Wp: 543 nm, FWHM 54 nm | Wp: 612 nm, FWHM 75 nm | 100:15:5 | 76 | 165, 195, 254 |
| Wp: 543 nm, FWHM 54 nm | Wp: 612 nm, FWHM 75 nm | 120:25:5 | 73 | 151, 233, 255 |
| Wp: 543 nm, FWHM 54 nm | Wp: 612 nm, FWHM 75 nm | 120:5:10 | 81 | 202, 89, 255 |
| Wp: 543 nm, FWHM 54 nm | Wp: 612 nm, FWHM 75 nm | 120:25:5 | 73 | 254, 107, 224 |
| Wp: 516 nm, FWHM 55 nm | Wp: 612 nm, FWHM 75 nm | 120:20:5 | 75 | 170, 149, 255 |
| Wp: 473 nm, FWHM 79 nm | | 100:20 | 77 | 8, 47, 255 |
| Wp: 612 nm, FWHM 75 nm | | 100:50 | 60 | 255, 81, 151 |
| Wp: 543 nm, FWHM 54 nm | | 100:70 | 53 | 0, 255, 142 |

Certain examples of various methods, devices, and/or systems disclosed herein may also include a control system. The control system may be operatively coupled to a device and may be operative to control operational features of the device such as but not limited to: a duration of illumination, exiting light color, light intensity, and/or light irradiance. The control system may include any now known or later developed microcontroller. The device may also include one or more sensors coupled to control system to provide feedback to control system. The sensor(s) may sense any parameter of a control environment of the device, including but not limited to: touch of the device, heat of a user's hand on the device, motion of a user, motion of a structure to which device is coupled, temperature, light reception, and/or presence of microorganisms on an exterior surface, etc. The sensor(s) may include any now known or later developed sensing devices for the desired parameter(s). The control system with the sensor(s) (and without) may control operation to be continuous or intermittent based on an external stimulus, and depending on the application.

Figure 15:
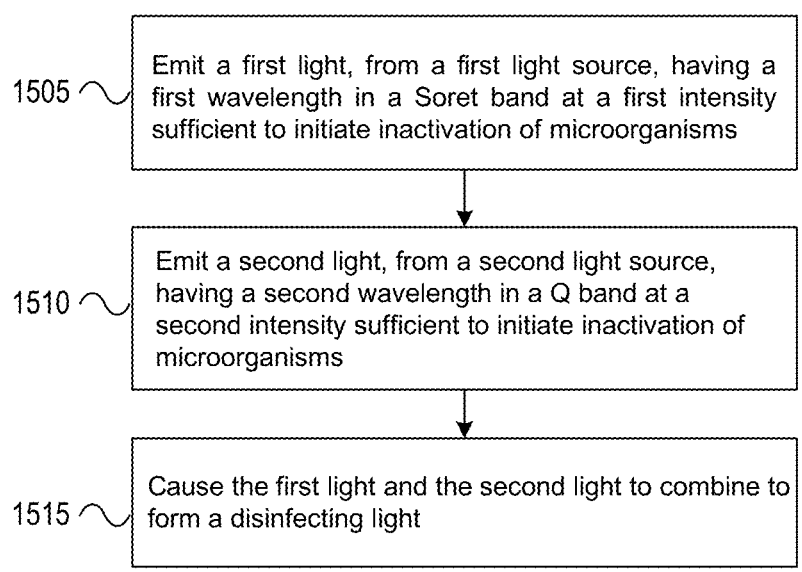
FIG. 15 shows an example method for generation of disinfecting white or non-white light, in accordance with one or more examples disclosed herein.

FIG. 15 shows an example method 1500 for generation of disinfecting white or non-white light in accordance with one or more examples disclosed herein. A lighting device, such as the lighting device 900, the lighting device 920, or the lighting device 930, or a combination of two or more lighting devices may be used to implement the method illustrated in FIG. 15. In other examples, a lighting device different from lighting devices described above may be used to implement the method illustrated in FIG. 15. At step 1505, the lighting device emits a first light, from a first light source, having a first wavelength in a Soret band at a first intensity sufficient to initiate inactivation of microorganisms. At step 1510, the lighting device emits a second light, from a second light source, having a second wavelength in a Q band at a second intensity sufficient to initiate inactivation of microorganisms. At step 1520, the light and the second light are combined to generate disinfecting light.

In some examples, the first light source and the second light source may be light converting materials the emit light based on incident light. In some examples, the first light source may be a light emitter and the second light source may be a light converting material that converts a portion of the first light from the first light source to emit the second light having the second wavelength. In some examples, the lighting device may be configured with a controller that may be used to vary the first intensity of the first light and the second intensity of the second light to control at least one of (i) color of the disinfecting light, (ii) color temperature of the disinfecting light, and/or (iii) an intensity of the disinfecting light.

Figure 16:
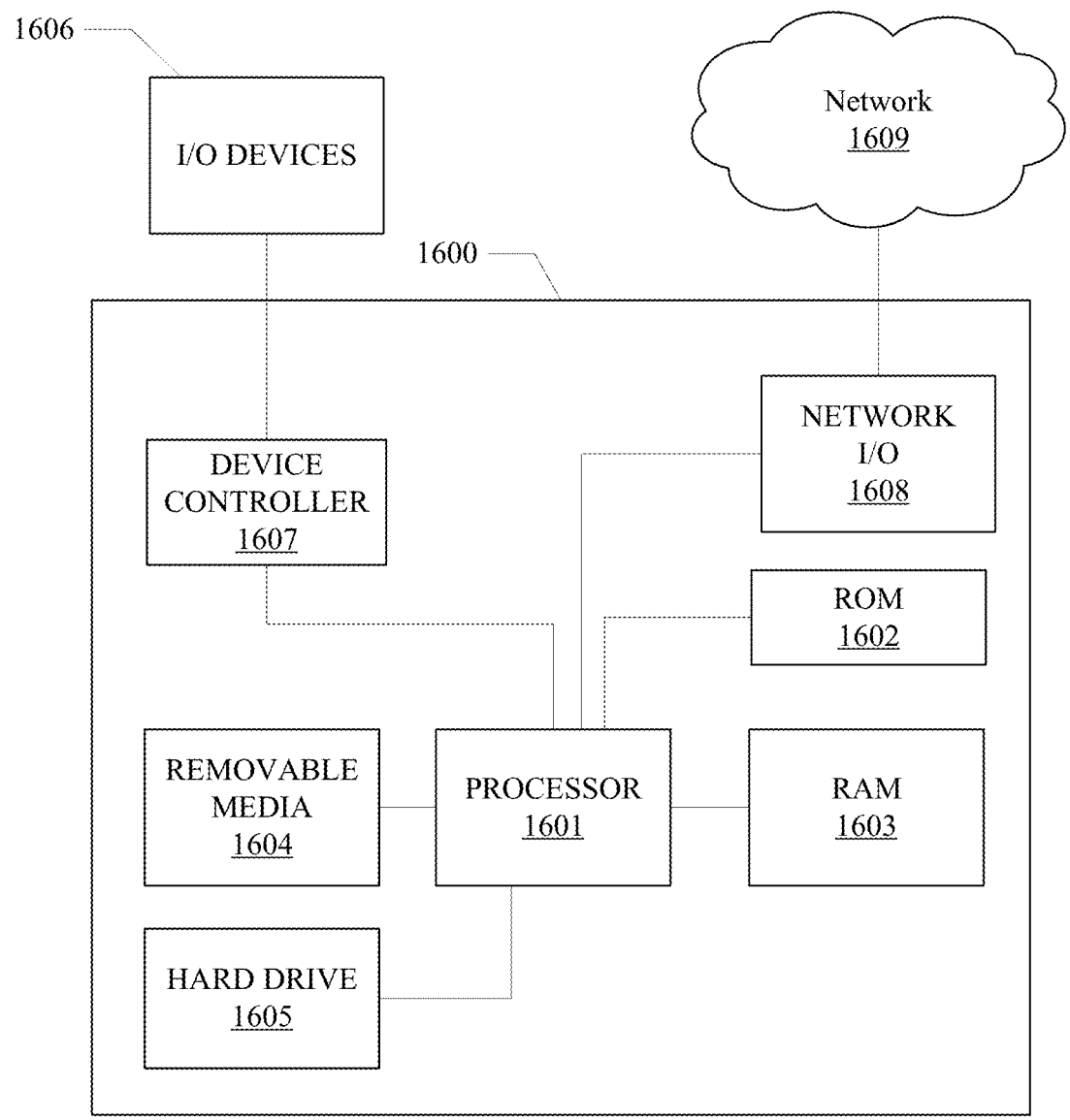
FIG. 16 shows an example computing device, that may be used for generation and/or control of disinfecting white light or non-white light, in accordance with one or more examples disclosed herein.

FIG. 16 illustrates an example computing device 1600, that may perform the method 1500, the functions of the control system describe herein, and/or any other computer, controller, or processor based function described herein. The computing device 1600 may include one or more processors 1601, which may execute instructions of a computer program to perform any of the features described herein. The instructions may be stored in any type of tangible computer-readable medium or memory, to configure the operation of the processor 201. As used herein, the term tangible computer-readable storage medium is expressly defined to include storage devices or storage discs and to exclude transmission media and propagating signals. For example, instructions may be stored in a read-only memory (ROM) 1602, random access memory (RAM) 1603, removable media 1604, such as a Universal Serial Bus (USB) drive, compact disk (CD) or digital versatile disk (DVD), floppy disk drive, or any other desired electronic storage medium. Instructions may also be stored in an attached (or internal) hard drive 1605. The computing device 1600 may include one or more input/output devices 1606, such as a display, touch screen, keyboard, mouse, microphone, software user interface, etc. The computing device 1600 may include one or more device controllers 1607 such as a video processor, keyboard controller, etc. The computing device 1600 may also include one or more network interfaces 1608, such as input/output circuits (such as a network card) to communicate with a network such as example network 1609. The network interface 1608 may be a wired interface, wireless interface, or a combination thereof. One or more of the elements described above may be removed, rearranged, or supplemented without departing from the scope of the present disclosure.

Modifications may be made as desired, to the above discussed examples, for different implementations. For example, steps and/or components may be subdivided, combined, rearranged, removed, and/or augmented; performed on a single device or a plurality of devices; performed in parallel, in series; or any combination thereof. Additional features may be added.

What is claimed is:

1. A light emitting device that inactivates microorganisms on a surface, the light emitting device comprising:
    a first light source operable to emit a first light having a first wavelength in a Soret band at a first intensity sufficient to initiate inactivation of microorganisms; and
    a light converting layer, in a path of the first light, configured to convert the first light to a second light having second wavelengths in a plurality of Q bands at second intensities sufficient to initiate inactivation of microorganisms;

wherein the first light and the second light combine to form a disinfecting light.

2. The light emitting device of claim 1, wherein a peak intensity of the first light is located in a wavelength range of 400 nm and 435 nm.

3. The light emitting device of claim 1, wherein peak intensities of the second light are located in two or more of (i) a first wavelength range of 497 nm-526 nm, (ii) a second wavelength range of 532 nm-563.5 nm, (iii) a third wavelength range of 566 nm-595 nm, or (iv) a fourth wavelength range of 593 nm-650.5 nm.

4. The light emitting device of claim 1, wherein the disinfecting light is a non-white light.

5. The light emitting device of claim 1, further comprising:
a controller configured to vary the first intensity and the second intensities to control at least one of (i) color of the disinfecting light, (ii) color temperature of the disinfecting light, or (iii) an intensity of the disinfecting light.

6. The light emitting device of claim 1, wherein the light converting layer comprises at least two or more of:
a first light converting material to convert a first portion of the first light to a third light having a third wavelength between 497 nanometers (nm) and 526 nm,
a second light converting material to convert a second portion of the first light to a fourth light having a fourth wavelength between 532 nm and 564 nm, and
a third light converting material to convert a third portion of the first light to a fifth light having a fifth wavelength between 566 nm and 595 nm, and
a fourth light converting material to convert a fourth portion of the first light to a sixth light having a sixth wavelength between 593 nm and 651 nm.

7. The light emitting device of claim 6, wherein the second light comprises two or more of the third light, the fourth light, the fifth light, and the sixth light.

8. A method of inactivating microorganisms, the method comprising:
emitting, from a first light source, a first light having a first wavelength in a Soret band at a first intensity sufficient to initiate inactivation of microorganisms;
converting, using a light converting layer in a path of the first light, the first light to a second light having second wavelengths in a plurality of Q bands at second intensities sufficient to initiate inactivation of microorganisms; and
causing the first light and the second light to combine to form a disinfecting light.

9. The method of claim 8, wherein a peak intensity of the first light is located in a wavelength range of 400 nm and 435 nm.

10. The method of claim 8, wherein peak intensities of the second light are located in two or more of (i) a first wavelength range of 497 nm-526 nm, (ii) a second wavelength range of 532 nm-563.5 nm, (iii) a third wavelength range of 566 nm-595 nm, or (iv) a fourth wavelength range of 593 nm-650.5 nm.

11. The method of claim 8, wherein the disinfecting light is a non-white light.

12. The method of claim 8, further comprising:
varying, via a controller, the first intensity and the second intensities to control at least one of (i) color of the disinfecting light, (ii) color temperature of the disinfecting light, or (iii) an intensity of the disinfecting light.

13. A light emitting device that inactivates microorganisms on a surface, the light emitting device comprising:
a light emitter operable to emit a first light having a first wavelength in a Soret band at a first intensity sufficient to initiate inactivation of microorganisms on the surface; and
a light converting layer arranged to be in a direct path of the first light and operable to convert the first light to a second light having second wavelengths in a plurality of Q bands at second intensities sufficient to initiate inactivation of microorganisms on the surface;
wherein the first light and the second light combine to form disinfecting light.

14. The light emitting device of claim 13, further comprising:
a controller configured to vary the first intensity and the second intensities to control at least one of (i) color of the disinfecting light, (ii) color temperature of the disinfecting light, or (iii) an intensity of the disinfecting light.

15. The light emitting device of claim 13, wherein the light converting layer comprises at least two or more of:
a first light converting material to convert a first portion of the first light to a third light having a third wavelength between 497 nm and 526 nm,
a second light converting material to convert a second portion of the first light to a fourth light having a fourth wavelength between 532 nm and 564 nm,
a third light converting material to convert a third portion of the first light to a fifth light having a fifth wavelength between 566 nm and 595 nm, and
a fourth light converting material to convert a fourth portion of the first light to a sixth light having a sixth wavelength between 593 nm and 651 nm;
wherein the second light comprises two or more of the third light, the fourth light, the fifth light, and the sixth light.

16. The light emitting device of claim 13, wherein:
a peak intensity of the first light is located in a wavelength range of 400 nm and 435 nm, and
peak intensities of the second light are located in two or more of (i) a first wavelength range of 497 nm-526 nm, (ii) a second wavelength range of 532 nm-563.5 nm, (iii) a third wavelength range of 566 nm-595 nm, or (iv) a fourth wavelength range of 593 nm-650.5 nm.

* * * * *